(12) United States Patent
Pinchuk et al.

(10) Patent No.: US 7,708,773 B2
(45) Date of Patent: May 4, 2010

(54) MODULAR STENT GRAFT EMPLOYING BIFURCATED GRAFT AND LEG LOCKING STENT ELEMENTS

(75) Inventors: Leonard Pinchuk, Miami, FL (US); Arthur Rosenthal, Wellesley, MA (US)

(73) Assignee: Gen4 LLC, Miami, FL (US)

( * ) Notice: Subject to any disclaimer, the term of this patent is extended or adjusted under 35 U.S.C. 154(b) by 457 days.

(21) Appl. No.: 11/336,175

(22) Filed: Jan. 20, 2006

(65) Prior Publication Data

US 2006/0178733 A1   Aug. 10, 2006

Related U.S. Application Data

(60) Provisional application No. 60/666,257, filed on Mar. 29, 2005, provisional application No. 60/646,078, filed on Jan. 21, 2005.

(51) Int. Cl.
*A61F 2/06* (2006.01)
*A61M 29/00* (2006.01)

(52) U.S. Cl. ............................ 623/1.35; 623/1.15

(58) Field of Classification Search ................. 623/1.15, 623/1.16, 1.17, 1.18, 1.19, 1.2, 1.21, 1.22, 623/1.11, 1.12, 1.13, 1.14, 1.35; 606/108
See application file for complete search history.

(56) References Cited

U.S. PATENT DOCUMENTS

| | | | |
|---|---|---|---|
| 4,619,641 A | 10/1986 | Schanzer | |
| 4,655,771 A | 4/1987 | Wallsten | |
| 5,383,925 A | 1/1995 | Schmitt | |
| 5,489,295 A | 2/1996 | Piplani et al. | |
| 5,562,725 A | 10/1996 | Schmitt et al. | |
| 5,575,817 A | 11/1996 | Martin | |
| 5,628,783 A | 5/1997 | Quiachon et al. | |
| 5,628,788 A | 5/1997 | Pinchuk | |
| 5,639,278 A | 6/1997 | Dereume et al. | |
| 5,697,969 A | 12/1997 | Schmitt et al. | |
| 5,855,601 A | 1/1999 | Bessler et al. | |
| 5,968,091 A | 10/1999 | Pinchuk et al. | |
| 6,152,956 A | 11/2000 | Pierce | |
| 6,162,245 A | 12/2000 | Jayaraman | |
| 6,165,212 A | 12/2000 | Dereume et al. | |
| 6,221,102 B1 | 4/2001 | Baker et al. | |
| 6,280,466 B1 | 8/2001 | Kugler et al. | |
| 6,344,052 B1 | 2/2002 | Greenan et al. | |
| 6,368,345 B1 * | 4/2002 | Dehdashtian et al. | 623/1.13 |
| 6,395,022 B1 | 5/2002 | Piplani et al. | |
| 6,409,756 B1 | 6/2002 | Murphy | |
| 6,458,153 B1 | 10/2002 | Bailey et al. | |
| 6,503,272 B2 | 1/2003 | Duerig et al. | |
| 6,517,573 B1 | 2/2003 | Pollock et al. | |
| 6,540,782 B1 | 4/2003 | Snyders | |
| 6,585,758 B1 * | 7/2003 | Chouinard et al. | 623/1.16 |
| 6,648,913 B1 | 11/2003 | Yee et al. | |
| 6,652,580 B1 | 11/2003 | Chuter et al. | |
| 6,660,033 B1 | 12/2003 | Marcade et al. | |
| 6,682,537 B2 | 1/2004 | Ouriel et al. | |

(Continued)

*Primary Examiner*—Vy Q Bui
(74) *Attorney, Agent, or Firm*—Gordon & Jacobson, PC

(57) ABSTRACT

A modular stent graft system and associated surgical methods are provided that incorporates an external stent-based locking mechanism to prevent disarticulation of the legs from the bifurcated graft as well as other features that overcome many of the difficulties of the prior art associated with delivering and securing the bifurcated grafts to the intended deployment site within the human aorta.

55 Claims, 20 Drawing Sheets

U.S. PATENT DOCUMENTS

| | | |
|---|---|---|
| 6,719,783 B2 | 4/2004 | Lentz et al. |
| 6,752,826 B2 | 6/2004 | Holloway et al. |
| 6,767,358 B2 | 7/2004 | Leonhardt et al. |
| 6,773,454 B2 | 8/2004 | Wholey et al. |
| 6,790,222 B2 | 9/2004 | Kugler et al. |
| 6,797,217 B2 | 9/2004 | McCrea et al. |
| 6,802,859 B1 | 10/2004 | Pazienza et al. |
| 6,830,585 B1 | 12/2004 | Artof et al. |
| 6,835,203 B1 | 12/2004 | Vardi et al. |
| 6,852,122 B2 | 2/2005 | Rush |
| 6,860,900 B2 | 3/2005 | Clerc et al. |
| 6,929,659 B2 | 8/2005 | Pinchuk |
| 6,929,661 B2 * | 8/2005 | Bolduc et al. ............... 623/1.35 |
| 7,326,237 B2 * | 2/2008 | DePalma et al. ............ 623/1.13 |
| 2002/0065546 A1 | 5/2002 | Machan et al. |
| 2003/0017775 A1 | 1/2003 | Sowinski et al. |
| 2004/0117004 A1 | 6/2004 | Osborne et al. |
| 2004/0162606 A1 | 8/2004 | Thompson |
| 2004/0215337 A1 | 10/2004 | Hain et al. |
| 2004/0236403 A1 | 11/2004 | Leonhardt et al. |

* cited by examiner

MODULAR STENT GRAFT EMPLOYING BIFURCATED GRAFT AND LEG LOCKING STENT ELEMENTS

This application claims priority from provisional application 60/666,257 filed Mar. 29, 2005 and from provisional application 60/646,078 filed Jan. 21, 2005, the contents of which are hereby incorporated by reference in their entirety.

BACKGROUND OF THE INVENTION

1. Field of the Invention

This invention relates broadly to intraluminal vascular implant devices. More particularly, this invention relates to intraluminal stents and grafts.

2. State of the Art

An abdominal aortic aneurysm (AAA) is a sac caused by an abnormal dilation of the wall of the descending aorta as it passes through the abdomen. The aorta is the main artery of the body, supplying blood to all organs and parts of the body except the lungs. It is typically described as three parts: the ascending aorta which rises upward from the left ventricle of the heart, the aortic arch which bends over to extend downward; and the descending aorta which passes down through the thorax and through the abdomen and finally divides into the two iliac arteries (which supply blood to the pelvis and lower extremities).

The aneurysm ordinarily occurs in the portion of the aorta below the kidneys. When left untreated, the aneurysm will eventually cause the sac to rupture with ensuing fatal hemorrhaging in a very short time. The repair of abdominal aortic aneurysms has typically required major abdominal surgery in which the diseased and aneurysmal segment of the aorta is removed and replaced with a prosthetic device, such as a synthetic graft.

As with all major surgeries, there are many disadvantages to the foregoing surgical technique, the foremost of which is the high mortality and morbidity rate associated with surgical intervention of this magnitude. Other disadvantages of conventional surgical repair include the extensive recovery period associated with such surgery; difficulties in suturing the graft to the aorta; the loss of the existing thrombosis to support and reinforce the graft; the unsuitability of the surgery for many patients, particularly older patients exhibiting co-morbid conditions; and the problems associated with performing the surgical procedure on an emergency basis after the aneurysm has already ruptured.

In view of the foregoing disadvantages of conventional surgical repair, catheter-based techniques have been developed for repairing abdominal aortic aneurysms by delivering an aortic stent graft to the aneurysm site via a catheter, and expanding the stent such that it secures the graft within the aorta. Stent grafts have been developed in order to not only simply hold open a passageway, but also to bridge across diseased vasculature from healthy vessel to healthy vessel.

Briefly, a stent graft is inserted over a guide wire, from the femoral or iliac artery and deployed within the aneurysm by a catheter, resulting in maintenance of blood flow from an aorta of acceptable (usually normal) caliber above to a portion of aorta or iliac artery(s) of acceptable (usually normal) caliber below the aneurysm. The aneurysm sac is thus excluded. Blood within this excluded sac thromboses and the aneurysm thus has no flow within it, presumably reducing the pressure and thus its tendency to burst.

Presently available stent grafts however have a number of problems. For example, current stent grafts are prone to persistent leakage around the area of the stent graft. Hence, pressure within the sac stays at or near arterial pressure and there is still a risk of rupture. There are 3 common types of such leakage. The first type is direct leakage around the stent graft. This can be persistent from the time of insertion because of poor sealing between the stent graft and vessel wall, or can develop later because the seal is lost. In addition, this problem can develop because the stent graft is not adequately fixated within the descending aorta, which allows the stent graft to migrate in relation to the aneurysm as the aneurysm grows, shrinks, elongates or shortens with time after treatment. The second type of leakage can occur because there are side arteries extending out the treated segment of blood vessel. Once the aneurysm is excluded by the device, flow can reverse within these blood vessels and continue to fill the aneurysm sac around the stent graft. The third type of leakage is direct leakage through the graft. Such leakage can occur in devices that use extensive amounts of metal in the stent and/or sutures to affix the graft to the stent. In these devices, the metal and/or sutures can abrade causing a rupture in the graft and leakage therefrom. Modular devices typically have connections that rely on friction alone. Such connects can disarticulate, thus causing leakage therefrom.

Some of the presently available stent grafts are also limited in their application to only select patients due to limitations in their design, including:

limited flexibility—which can cause difficulties during delivery and possible incompatibility for patients with a tortuous iliac artery, a tortuous aorta, and/or a tortuous aneurysm;

limited conformity with changing aneurysm shape—which can cause leakage;

required infrarenal fixation (i.e., fixation below the renal arteries)—which results in incompatibility for patients with a short infrarenal neck (i.e., a relatively short distance of healthy vasculature below the renal arteries);

limited sizes—which results in incompatibility for patients with an aneurysm size different from such limited size; and/or required delivery by a large diameter catheter—which results in incompatibility for patients with an iliac artery and/or aorta that is tortuous or possibly heavily calcified and diseased (which are frequently associated with AAA).

Thus, there remains a need in the art for an improved stent graft that does not suffer from the limitations of the prior art designs.

SUMMARY OF THE INVENTION

It is therefore an object of the invention to provide a stent graft system with improved flexibility such that it is compatible for patients with a tortuous iliac artery, a tortuous aorta, and/or a tortuous aneurysm.

It is another object of the invention to provide such a stent graft system that conforms to changing aneurysm shapes over time, and thus aids in mitigating leakage resulting therefrom.

It is a further object of the invention to provide a stent graft system that utilizes suprarenal fixation (i.e., fixation above the renal arteries) to accommodate patients with a short infrarenal neck (i.e., a relatively short distance of healthy vasculature below the renal arteries).

It is also an object of the invention to provide a stent graft system that can readily be adapted to have different sizes, thereby providing accommodation for patients over a wide variety of aneurysm sizes and shapes.

It is an additional object of the invention to provide a stent graft system that can be delivered by a small diameter catheter, thereby accommodating patients with an iliac artery and/or aorta that is tortuous or possibly heavily calcified and diseased.

In accord with these objects, which will be discussed in detail below, a modular stent graft system and associated surgical methods are provided that overcome many of the difficulties of the prior art associated with delivering and securing the bifurcated grafts to their intended deployment site in the human aorta. The modular stent graft system employs an improved stent-based locking mechanism to prevent disarticulation of the legs from the bifurcated graft. Moreover, by providing a stent graft in the form of modular components that can be individually selected and assembled together, the present invention permits more accurate sizing of the components to the individual patient.

In a preferred embodiment, the stent graft employs a laser cut stent formed from Nitinol (or other shape memory metal), which eliminates metal to metal wear at stress points. It also preferably employs a polymeric adhesive (or filler) that binds the supporting stent to the bifurcated graft. This feature eliminates reliance on sutures and allows pull down. Moreover, the polymeric adhesive couples motion of the bifurcated graft with the motion of the stent to prevent abrasion. The stent graft also employs active fixation to the aorta wall above the renal arteries (e.g., suprarenal fixation) together with barbs that are designed to prevent perforation of the aorta. The flexible suspenders of the stent prevent jailing of renal arteries and together with the suprarenal fixation can accommodate aneurysms with infrarenal necks that are less than 5 mm in length. The flexibility of the suspenders of the stent allow for bendability, which can be up to 45 degrees in the renal area and up to 60-90 degrees below the renal area. These features allow the stent graft to accommodate tortuous aneurysms.

Moreover, the leg grafts preferably employ a stretchable and compressible polymeric tube-in-tube structure with universal bendability, which accommodate morphing aneurysms.

The stent graft system and the delivery catheter assemblies described herein also provide for precise and controllable placement in the aorta. In addition, the stent graft system is simple and inexpensive to manufacture (e.g., not labor intensive).

Additional objects and advantages of the invention will become apparent to those skilled in the art upon reference to the detailed description taken in conjunction with the provided figures.

DETAILED DESCRIPTION OF THE PREFERRED EMBODIMENTS

As used herein, the term "distal" is generally defined as in the direction away from a user of the system/apparatus/device. Conversely, "proximal" generally means in the direction toward the user of the system/apparatus/device.

Figure 1:
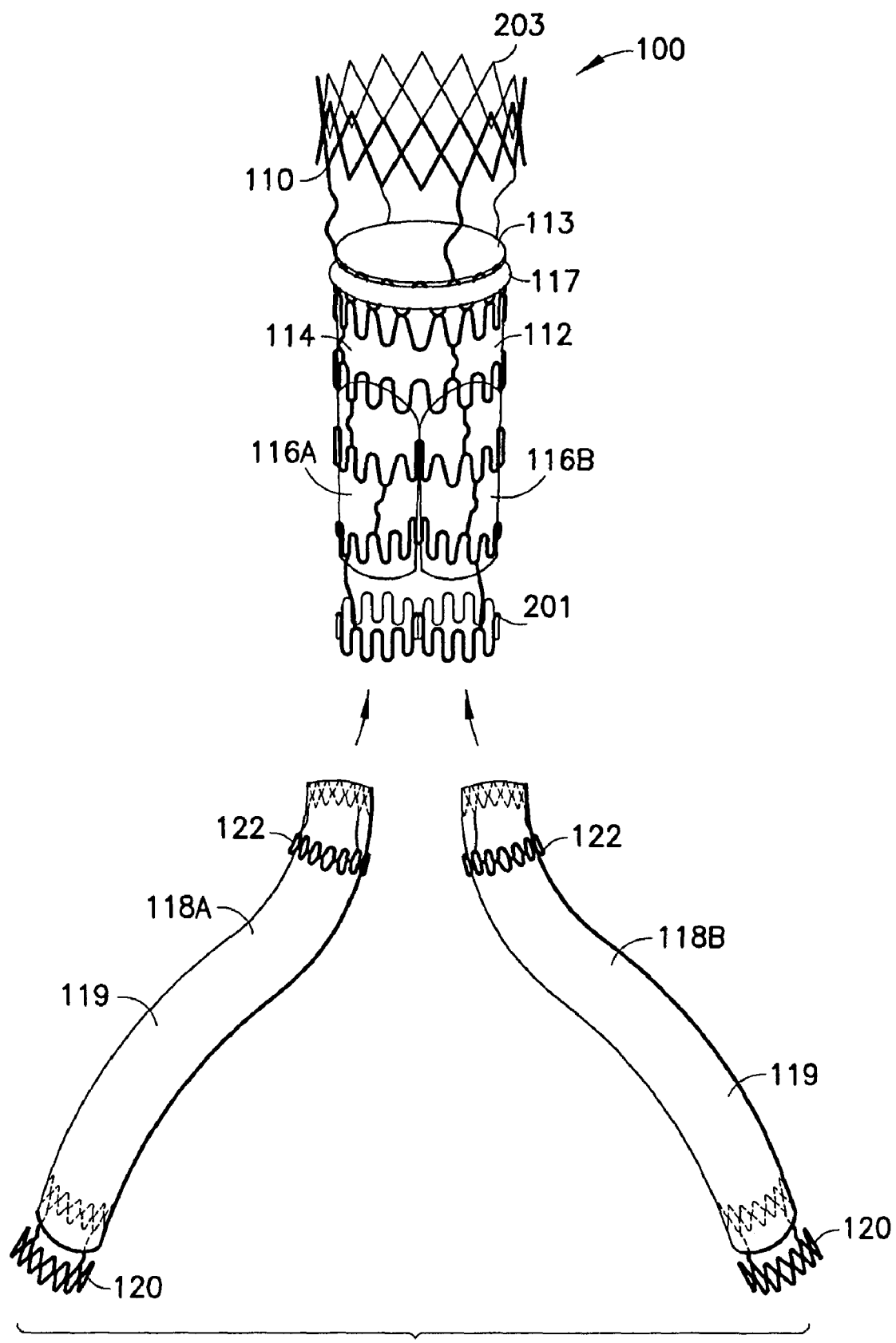
FIG. 1 is a partially exploded view of a modular stent graft system in accordance with the present invention.
Figure 2:
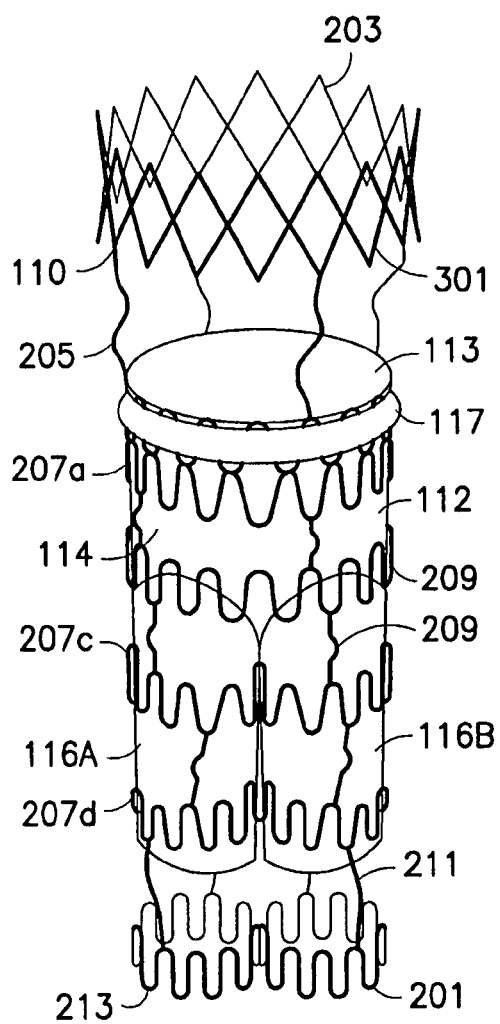
FIG. 2 is a schematic view of the primary stent, primary graft and seal of the system of FIG. 1.

Turning now to FIGS. 1 and 2, there is shown a modular stent graft system 100 in accordance with the present invention. As used herein, the term "modular" refers to the fact that system 100 includes a number of individual components which may be separately delivered by catheter(s) to the aneurysm site and then interconnected with one another in situ to form the stent graft. The system 100 includes: a primary stent 110 (FIGS. 2, 8, 9); a primary graft 112 with a top section 113, a bifurcated hip section 114 and two pant legs 116A, 116B; a seal 117; and two leg grafts 118A, 118B each with a proximal fixation stent 120 and a distal fixation stent 122. The primary stent 110 is adapted to hold the aorta open while supporting the primary graft 112 and the two leg grafts 118A, 118B. The primary graft 112 and the two leg grafts 118A, 118B provide a passageway for the flow of blood therethrough (e.g., from an entrance in the aorta below the renal arteries to exits in the iliac arteries). The seal 117 is operably disposed between a healthy section of the aorta wall and an annular part (e.g., segment 207a) of the primary stent 110. The seal 117 fills voids around plaque and prevents leakage of blood around the outside of the distal end of the primary graft 112. The seal 117 is preferably realized from a soft porous foam with pores that allow tissue ingrowth over time for improved sealing. In addition, the foam is preferably loaded with a drug such as a growth factor or other drug that allows cellular growth and proliferation as is known in the art. In addition, the foam may be surface coated with an agent that promotes tissue ingrowth such as titanium and the like. These components are preferably fabricated separately in a range of sizes sufficient to accommodate the arterial morphology which the surgeon is likely to face in the vast majority of patients, and then assembled in a selected size combination depending upon the arterial morphology presented by the patient.

The primary stent 110 is preferably made from a laser machined shape memory metal such as nitinol or Elgiloy or any other medical grade metal suitable for stents, stent-grafts and the like. With such a laser machine design, it is possible to avoid metal-on-metal contacts together with the abrasion and leakage potential that results therefrom. Alternatively, the primary stent 110 can be made using wire forms with and without welding.

The primary stent 110 consists of a proximal end 201 opposite a distal end 203. The distal end 203 contains an annular band of diamond shaped elements with adjacent elements sharing a common junction point. This band of diamond shaped elements is herein called a fixation ring 205. Alternatively, the fixation ring 205 can also be comprised of hexagonal shaped or zig-zag shaped elements, etc.

Figure 3A:
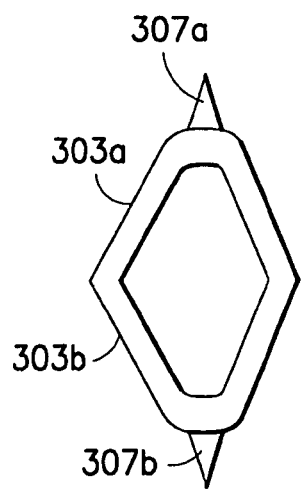
FIG. 3A is a front schematic view of a diamond-shaped element of the fixation ring of the primary stent of FIGS. 1 and 2.
Figure 3B:
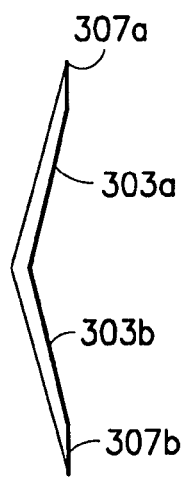
FIG. 3B is a side schematic view of the diamond-shaped element of FIG. 3A.

As shown in FIGS. 3A and 3B, each diamond shaped element 301 is formed in a geometry such that its upper V-shaped portion 303a extends upward (distally) and radially outward at an acute angle relative to the vertical direction 305, while its lower V-shaped portion 303b extends downward (proximally) and radially outward at an acute angle relative to the vertical direction 305, thereby forming a waist in the middle. The apices of the upper and lower V-shaped portions 303a, 303b include barbs 307a, 307b that project therefrom as shown. The purpose of the angle of the upper V-shaped portion 303a and corresponding barb 307a is to contact the inner wall of aorta in order to prevent the primary stent 110 from moving distally in the aorta. Similarly, the purpose of the angle of the lower V-shaped portion 303b and corresponding barb 307b is to contact the inner wall of aorta in order to prevent the primary stent 100 from moving proximally in the aorta. In this manner, the V-shaped portions 303a, 303b and corresponding barbs 307a, 307b fixate the primary stent 100 in place against the inner wall of the aorta. The length and orientation of the barbs 307a, 307b are designed such that barbs 307a, 307b do not perforate the wall of the aorta. The openings afforded by the diamond shaped elements 301 allow for tissue ingrowth and permanent fixation.

Referring back to FIGS. 1 and 2, a plurality of (preferably, at least four) flexible suspenders or connectors 205 hang from the fixation ring 203 and attach the fixation ring 203 to multiple segments (207a, 207b, 207c, 207d) that support the primary graft 112. Segment 207a consists of a pair of connected annular strut elements that are disposed adjacent to one another along the vertical direction and that are operably disposed at or near the distal end of the top section 113 of the primary graft 112 to conform to and support the top section 113. Segment 207b consists of an annular strut element operably disposed adjacent the bifurcated hip section 114 of the primary graft 112 to thereby conform to and support the bifurcated hip section 114. Segment 207c consists of a substantially annular strut element that pinches in at two opposing points toward the central axis of the primary stent 110. It is operably disposed adjacent the upper part of the pants 116A, 116B of the primary graft 114 to thereby conform to and support the pants 116A, 116B. Segment 207d consists of a strut element that pinches in at two opposing points toward the central axis of the primary stent 110 to form two smaller diameter sections that are spaced apart from one another along the radial direction (perpendicular to the central axis). These two smaller diameter sections are operably disposed adjacent the lower part of the respective pants 116A, 116B to thereby conform to and support the pants 116A, 116B. The segments 207a, 207b, 207c, 207d are spaced apart from one another along the longitudinal axis of the primary stent 110 by a plurality of flexible suspenders 209. The length (and/or possibly the number of suspenders) between adjacent segments may vary depending upon the desired shape and flexibility. In the preferred embodiment, there at least four suspenders between segments.

A plurality of (preferably, at least 4) flexible suspenders or connectors 211 hang from the lower graft-supporting segment 207d and attach it to a stent segment 213 that supports the legs 118A, 118B. Segment 213 consists of a strut element that pinches in at two opposing points toward the central axis of the primary stent 110 to form two smaller diameter sections that are spaced apart from one another along the radial direction (perpendicular to the central axis), which is similar to the geometry of segment 207d. However, these two smaller diameter sections are operably disposed adjacent the distal part of the respective legs 118A, 118B to thereby conform to and support the legs 118A, 118B.

The top section 113, hip section 114, and pants 116A, 116B of the primary graft 112 preferably have a profile whose diameters are less than the diameter of the fixation ring 203. Moreover, the shape and size of the sections of the primary graft 112 can readily be adapted such that the primary graft 112 tapers along any part of its length from its distal end to its proximal end. Likewise, the diameters of the fixation ring 203 and the segments of the primary stent 110 can readily be adapted to conform and support such geometries.

The primary graft 112 is formed from a biocompatible material having sufficient strength to withstand the surgical implantation procedure described more fully below and to withstand the blood flow and other biomechanical forces which are exerted on modular system 100 is use. Such materials may include, for example, PET (polyethylene terephthalate), PTFE (polytetrafluoroethylene), expanded polytetrafluoroethylene (ePTFE), polyester materials such as DACRON®, other textiles such as nylon, or polyester material coated with PTE, PTFE, ePTFE, or silicon. It is preferred that the primary graft 112 be formed from woven or knitted materials. To reduce the bulk and facilitate the intraluminal delivery, the primary graft 112 preferably has a thickness of about 0.005 to 0.020 inches, and preferably approximately 0.010 inches, although it will be appreciated that the present invention can be practiced using materials which are greater than 0.020 inches in thickness, including conventional graft materials.

The material forming the trunk and the legs can be similar in construction; i.e., they can be knits, braids, weaves, non-weaves, foams, expanded materials, and the like. The trunk, being of a larger diameter can be constructed of material having a lesser porosity than the legs so as to prevent leakage of blood through the wall. In fact, the trunk can be non-porous. The legs, on the other hand, being of a lesser diameter than the trunk are preferably porous to allow tissue ingrowth and thereby maintain patency. Tissue ingrowth in the trunk is not usually achieved due to the lack of juxtaposition of the trunk with live tissue in the vacant aneurysm. At the large diameters of the trunk, tissue ingrowth is not entirely necessary to maintain patency.

Figure 4:
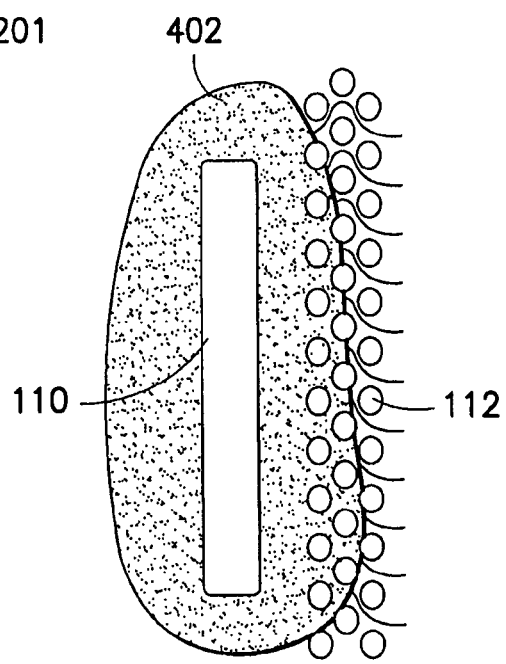
FIG. 4 is a cross-sectional schematic view the composite structure formed by bonding the strut elements of the primary stent to the material of the primary graft with a polymeric adhesive in accordance with the present invention.

The segments 207a, 207b, 207c, and 207d of the primary stent 110 are external to and envelop the primary graft 112 as best shown in FIGS. 1 and 2. Alternatively, the graft 112 may be woven within a stent 110 or exterior to a stent 110. In order to provide structural support, the segments 207a, 207b, 207c and 207d may be secured to the primary graft 112 by sutures or other suitable coupling means. In the preferred embodiment, the struts of the segments 207a, 207b, 207c, 207d are bonded to the material of the primary graft 112 by a biocompatible polymeric adhesive (or filler) 402 as best shown in FIG. 4. The hardness of the polymeric adhesive 402 can be controlled to allow the adhesive 402 to couple the motion of primary graft 112 with the motion of the primary stent 110, thereby preventing abrasion and leakage that may result therefrom. The polymeric adhesive 402 also couples the stent 110 to the graft 112 in a manner that allows the two components to pull down together. This feature allows the stent 110 and graft 112 to conform to changes in the shape of the aneurysm over time, which aids in preventing leakage that might otherwise result. This feature also avoids the use of sutures, thereby avoiding abrasion and the potential for leakage that might result therefrom. The hardness of the adhesive 402 as well as the bendability of the primary stent 110 is also preferably controlled to provide for flexibility of the resulting composite structure (e.g., adhesive/metal strut element/graft). The bendability of the primary stent 110 is primarily dictated by the thickness and geometry of the suspenders 205,

209, 211. In the preferred embodiment, the resulting composite structure is capable of bending up to 60 degrees (without collapse) to accommodate a tortuous aneurysm.

An example of a suitable material for the adhesive 402 is a polyolefinic copolymer material having a tri-block polymer backbone comprising polystyrene-polyisobutylene-polystyrene, which is herein referred to as "SIBS". Non-cross linked high molecular weight polyisobutylene (PIB) is a soft putty-like material with a Shore hardness less than 20A. When copolymerized with polystyrene, it can be made at hardnesses ranging up to the hardness of polystyrene, which has a Shore hardness of 100D. Thus, depending on the relative amounts of styrene and isobutylene, the SIBS material can have a range of hardnesses from as soft as Shore 10A to as hard as Shore 100D. In this manner, the SIBS material can be adapted to have the desired hardness qualities. Details of the SIBS material is set forth in U.S. Pat. Nos. 5,741,331; 6,102,939; 6,197,240; 6,545,097, which are hereby incorporated by reference in their entirety.

The SIBS material of the filler 402 may be polymerized under control means using carbocationic polymerization techniques such as those described in U.S. Pat. Nos. 4,276,394; 4,316,973; 4,342,849; 4,910,321; 4,929,683; 4,946,899; 5,066,730; 5,122,572; and Re 34,640, each herein incorporated by reference in its entirety. The amount of styrene in the copolymer material is preferably between about 12 mole percent to 35 mole percent for the desired hardness. The styrene and isobutylene copolymer materials are preferably copolymerized in solvents.

Alternatively, the adhesive 402 may include a polyisobutylene-based material capped with a glassy segment. The glassy segment provides hard domains for the elastomeric polyisobutylene and is non-reactive in the body. The glassy segment preferably does not contain any cleavable group which will release in the presence of body fluid and cause toxic side effects. The glassy segment can be a vinyl aromatic polymer (such as polystyrene, α-methylstyrene, or a mixture thereof), or a methacrylate polymer (such as methylmethacrylate, ethylmethacrylate, hydroxymethalcrylate, or a mixture thereof). Such materials preferably have a general block structure with a central elastomeric polyolefinic block and thermoplastic end blocks. Even more preferably, such materials have a general structure:

BAB or ABA (linear tri-block),
B(AB)n or A(BA)n (linear alternating block), or
X-(AB)n or X-(BA)n (includes di-block, tri-block and other radial block copolymers),
where A is an elastomeric polyolefinic block, B is a thermoplastic block, n is a positive whole number and X is a starting seed molecule.

Such materials may be star-shaped block copolymers (where n=3 or more) or multi-dendrite-shaped block copolymers.

In yet other alternatives, the polymeric material adhesive 402 may be silicone rubber, polyurethane (preferably polycarbonate urethane), polyolefin (preferably polyisoprene, polybutadiene (hydrogenated), polyethylene butylenes (SEBS)), etc.

The adhesive can be applied by spray coating, dip coating, submerging the stent in a fluidized bed, vapor depositing, sputter coating or printing the adhesive on each strut element. The preferred method is to spray coat with multiple layers where the coating is dried between layers.

The sealant is a polymer used to fill the interstices of the fabric comprising the trunk and the legs. The sealant can be made from a degradable material such as gelatin, collagen, polysaccharide, polylactic acid-containing hydrogels, polypeptides, and the like. Alternatively, the sealant can be a non-degradable micro-porous meshwork comprised of ePTFE, SIBS and the like.

Figure 5:
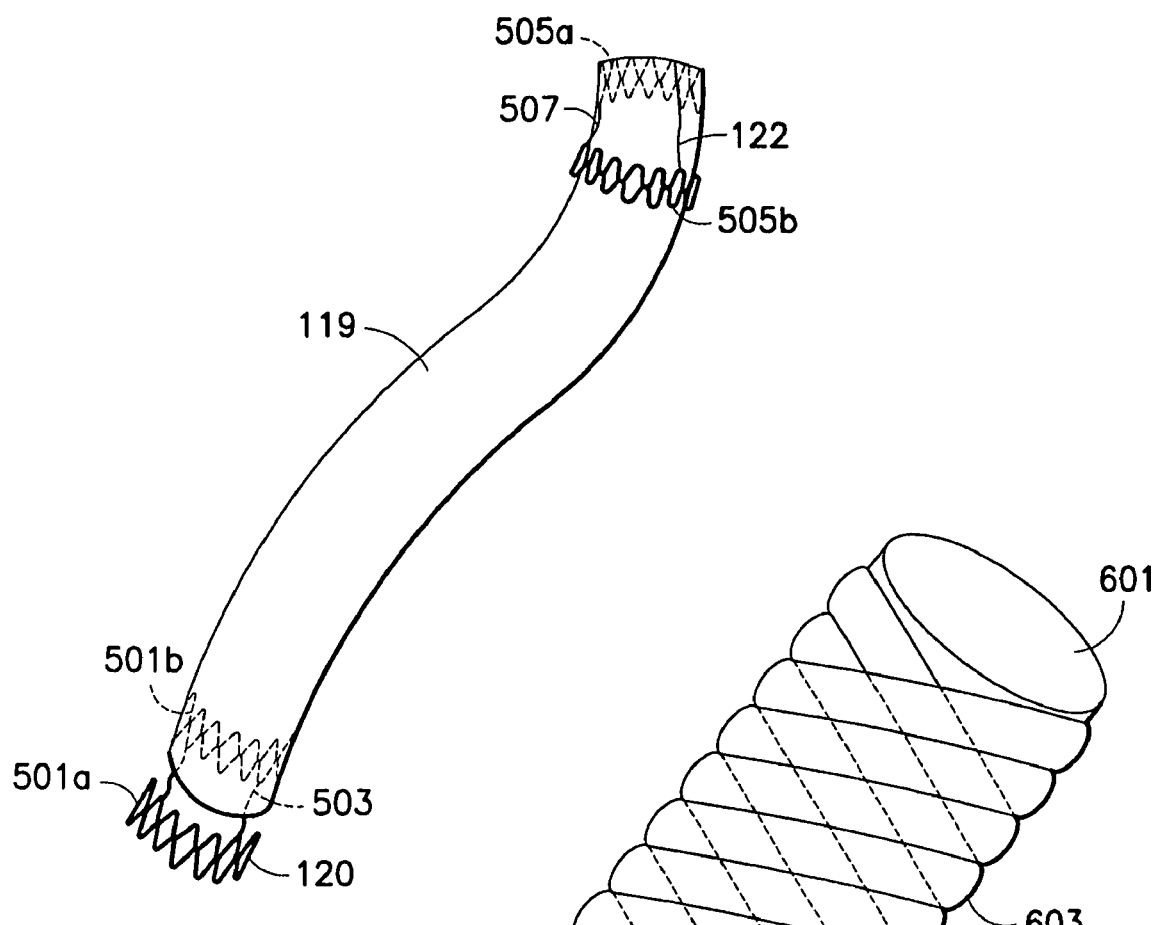
FIG. 5 is a schematic view of a leg graft of the system of FIG. 1.

The graft legs 118A, 118B of the modular stent-graft system 100 each include an elongate graft 119 (shown in FIG. 5) with a proximal fixation stent 120 and a distal fixation stent 122. The proximal fixation stent 120 includes two annular strut elements 501a, 501b spaced apart by a plurality of (preferably, at least 4) suspenders 503. The strut element 501b is disposed within the lumen of the proximal end of the graft 119 and affixed thereto, preferably by frictional forces due to its self-expanding nature and possibly other securing means. The suspenders 503 extend from the lumen and connect to the strut element 501a such that it is proximally disposed relative to the proximal end of the graft 119 as shown. In this configuration, the external strut element 501a provides active fixation to the wall of the iliac artery during use. The distal fixation stent 122 includes two annular strut elements 505a, 505b spaced apart by a plurality of (preferably, at least 4) suspenders 507. The strut element 505a is disposed within the lumen at the distal end of the graft 119 and affixed thereto, preferably by frictional forces due to its self-expanding nature and possibly other securing means. The suspenders 505 extend proximally from the end of the lumen and connect to the external strut element 505b as shown. During use, the internal strut element 505a ensures that the distal end of the leg graft 119 to is sealed to the proximal end of the corresponding pant (116A or 116B) of the primary graft 112, while the external strut element 505b is disposed distally relative to segment 213 which together cooperate to provide an interlocking mechanism that aids against disarticulation of the respective leg graft from the primary graft and the leakage that would result therefrom. These features are best shown in the assembled view of FIG. 7.

The elongate graft leg 119 is formed from a biocompatible material having sufficient strength to withstand the surgical implantation procedure described more fully below and to withstand the blood flow and other biomechanical forces which are exerted on modular system 100 is use. Such materials may include, for example, PET (polyethylene terephthalate), PTFE (polytetrafluoroethylene), expanded polytetrafluoroethylene (ePTFE), polyester materials such as DACRON®, other textiles such as nylon, or polyester material coated with PTE, PTFE, ePTFE, or silicon.

Figure 6:
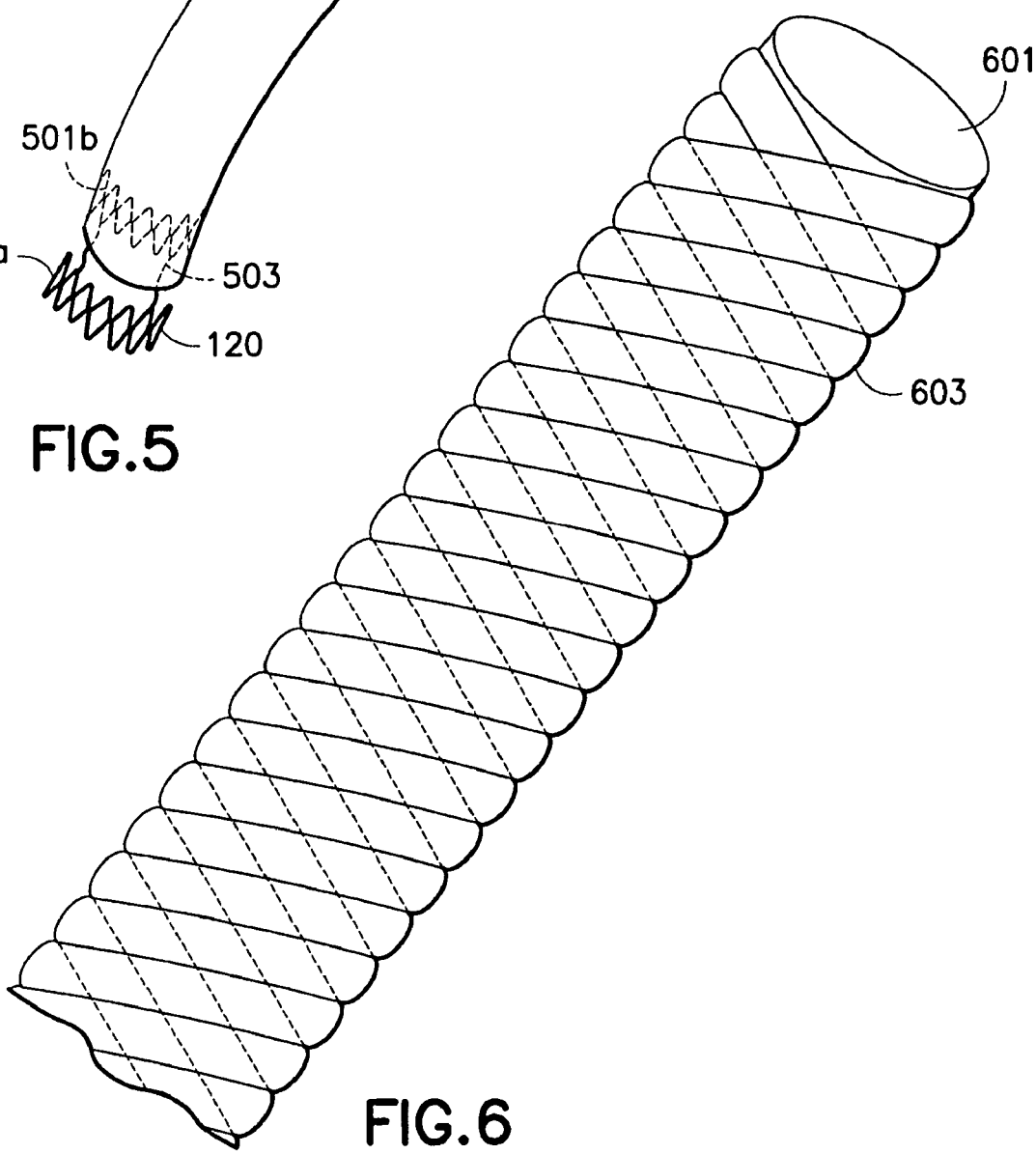
FIG. 6 is a schematic view of an elongate tube-in-tube polymeric graft structure in accordance with the present invention.

In the preferred embodiment, the elongate graft 119 is formed from two concentric tubular bodies 601, 603 that are bonded together as shown in FIG. 6. The inner tube 601 is formed of a flexible biocompatible material (preferably a knitted or braided fabric with a pore size and density that prohibits blood flow therethrough) that allows for pull down such that the length and diameter of the inner tube 601 changes in response to axial forces applied to the ends of the body 601. The outer tube 603 is a biocompatible polymeric material braided with Wallsten-type pattern (preferably of an inert polymer such as PET or FEP) that also allows for pull down such the length and diameter of the outer tube 603 changes in response to axial forces applied to the ends of the body 603. As compared to the structure of the inner tube 601, the Wallsten-type braid pattern of the outer tube provides increased resistance to radial forces applied thereto such that the outer tube 603 provides increased resistance to collapse in response to such radial forces. The Wallsten-type braid pattern of the outer tube 603 employs flexible polymeric thread elements each of which extend in a helical configuration about the central axis of the body 603. Some of the thread elements are wound in a clockwise direction, while other thread elements are wound in a counter clockwise direction.

The windings are displaced relative to one another axially and cross over the opposite windings in an interlocking pattern. Details of the Wallsten-type braid structure are described in U.S. Pat. No. 4,655,771 to Wallsten, herein incorporated by reference in its entirety. Preferably, the diameter of the inner tube 601 in its unloaded-relaxed state substantially matches (or is slightly less than) the diameter of the outer tube 601 in its unloaded-relaxed state. The outer tube 603 is bonded to the inner tube 601 by an adhesive (preferably, a polymer based adhesive). Preferably, a SIBS-based material is used to bond the outer tube 603 to the inner tube 601. Once bound, the length and diameter of both the inner tube 601 and the outer tube 603 can be controlled by application of radial forces to the ends of the resultant inner/outer tube structure. In the preferred embodiment, the length and diameter of the elongate graft 119 can stretch and compress by a factor of at least 20 percent over its unloaded-relaxed state. This feature allows the graft 119 to accommodate morphing of the aneurysm over time and thus aids in reducing leakage that might result therefrom. In addition, the flexible nature of the tubular structure allows for omni-directional bend angles (e.g., angles greater than 180 degrees) of the graft 119. This feature allows the graft 119 to accommodate tortuous aneurysms. Moreover, the polymer-base structure of the graft 119 avoids metal-on-metal wear and thus aids in reducing leakage that might result therefrom.

In the preferred embodiment, the concentric tubular bodies 601, 603 are bonded together as follows. First, an adhesive is applied to the outer surface of the inner tube 601, for example by spraying, dipping, or coating. Alternatively, the adhesive can be applied to the inner surface of the outer tube 603. The outer tube 603 is then placed over the coated inner tube 601. This can be accomplished by pulling the ends of the inner tube 601 to pull down the inner tube 601 and reduce its diameter, sliding the outer tube 603 over the stretched inner tube 601, and releasing the inner tube 601. Heat shrink tubing is then placed over the tube-in-tube structure. The shrink temperature of heat shrink tubing is above the melting point of the adhesive and below the melting point of the material of the inner tube 601 and outer tube 603. The resulting structure is heated in an oven at the shrink temperature, thereby shrinking the heat shrink tubing and melting the adhesive. The structure is allowed to cool and the heat shrink tubing is removed. The cooling causes the adhesive to permanently bind the outer tube 603 to the inner tube 601.

Figure 7:
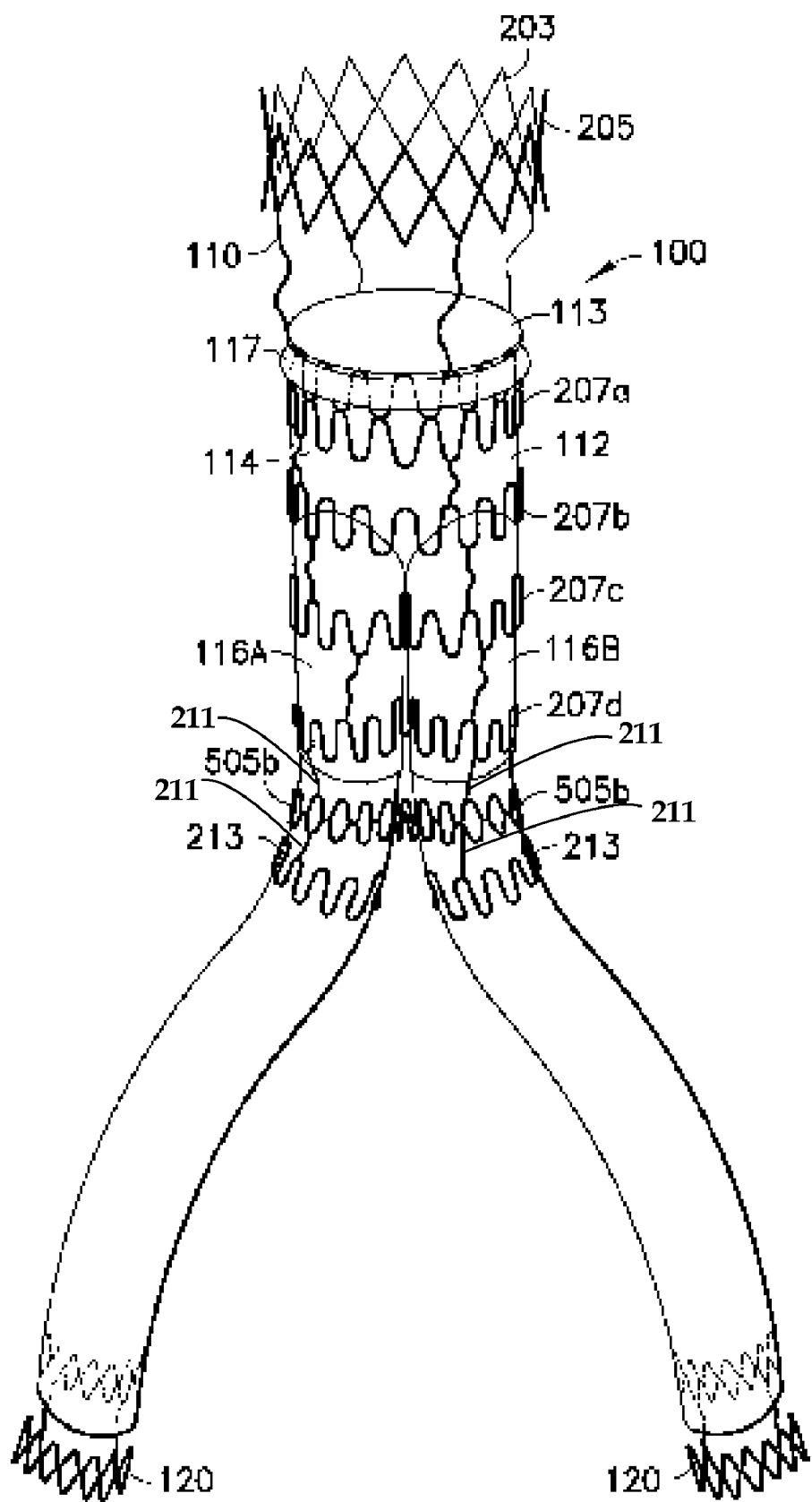
FIG. 7 is a schematic view of the modular stent graft system of FIG. 1 in its in situ assembled state.
Figure 8:
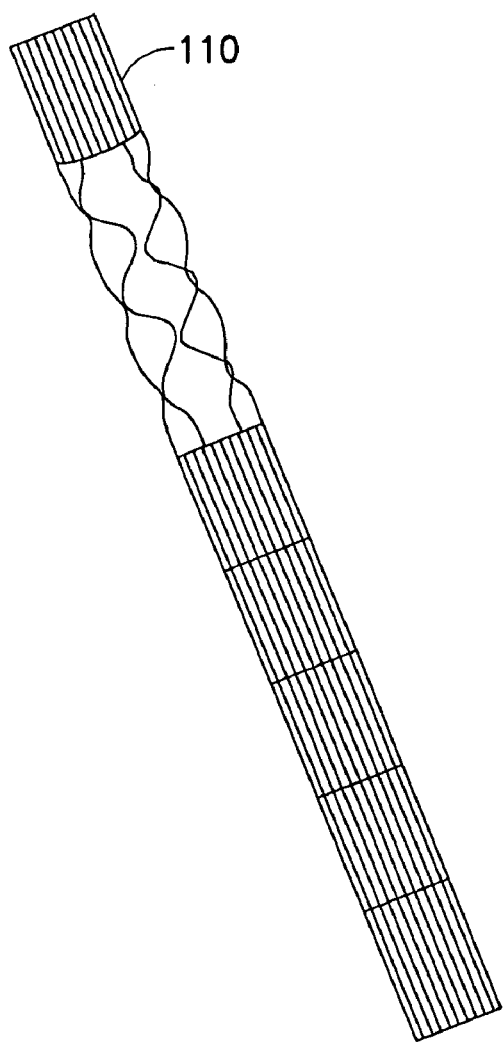
FIG. 8 is a photograph of the primary stent of FIG. 7 in its collapsed state.
Figure 9:
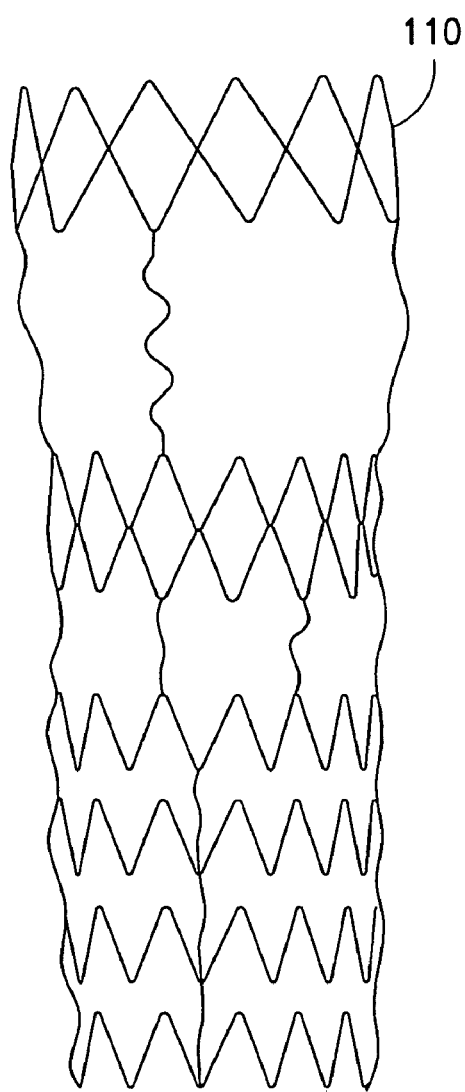
FIG. 9 is a photograph of the primary stent of FIG. 7 in its expanded state.

The primary stent 110, the primary graft 112, the seal 117, and the two leg grafts 118A, 118B are each radially expandable from a collapsed condition in which the circumferences thereof are minimized to an expanded condition in which the circumferences of each of these components approaches a predetermined maximum circumference. Such collapsibility/expandability allows the components to be delivered to the site of the AAA intraluminally. As will be described in more detail below, each component is normally held in the collapsed condition by the sheath of a catheter during delivery. Once properly located, the components are deployed from the catheter and radially expanded to the desired circumference. The legs grafts 118A, 118B are separately delivered by intraluminal techniques to the aneurysm site (or in proximity thereto) wherein their distal ends are interconnected with the respective pants 116A, 116B of the primary graft 112 and locked in place by the stent elements 213/505b as described above. The proximal ends of the leg grafts 118A, 118B are actively fixated in place in the iliac arteries by stent elements 120. In this manner the modular bifurcated graft is formed in situ as shown in FIG. 7. Photographs of the primary stent in its collapsed condition and expanded condition are shown in FIGS. 8 and 9, respectively.

The components 110, 112, 118A, 118B may include one or more radiomarkers (not shown) for identifying positions during surgical implantation. Such radiomarkers are conventional in the art and, when viewed under fluoroscopy, enable the surgeon to identify and properly locate the component(s). Thus, radiomarkers may be formed from biocompatible metals, such as, for example, stainless steel or platinum-iridium, which are radioopaque, or from radioopaque polymers.

Once the proper sizes for the various components of modular system 100 have been selected, the components are preferably preloaded into one or more disposable delivery catheter assemblies which then may be used by the surgeon to intraluminally introduce the components into the patient and to assemble same to one another in the form of a bifurcated graft. An exemplary delivery catheter assembly and a surgical method based thereon is described below with respect to FIGS. 10A-10O. A typical AAA is shown in which the wall of the aorta 900 is weakened and forms a bulge 902 in the region between the renal arteries 904a, 904b and the point at which the aorta 900 branches into the right iliac artery 906 and the left iliac artery 908.

The delivery catheter assembly 1000 includes an elongated tubular outer sheath 1002, which is preferably formed from a conventional polymer which is sufficiently flexible that it will readily bend as the catheter assembly 1000 is fed through the arterial path during the intraluminal surgical procedure. Typical materials for forming the sheath 1002 include biocompatible polymers, for example, nylon, TEFLON polytetrafluoroethylene, polyethylene, polyurethane and nylon copolymer, and the like. The distal end 1004 of the sheath 1002 may include a radiomarker (not shown) for readily identifying and locating the end 1002 under fluoroscopy. At its proximal end (not shown) the sheath 1002 may be fitted with any number of conventional accessories, such as a hand grip (and/or a Y-connector, hemostasis valve, or stopcock).

The catheter assembly 1000 also includes a tip 1006 which may be formed from a biocompatible polymer, such as polyurethane, TEFLON, polytetrafluoroethylene, nylon or the like. The tip 1006 may have a radiomarker (not shown) formed or assembled thereon for readily identifying and locating the tip 1006 under fluoroscopy. The proximal end of the tip 1006 preferably has an outer diameter which is larger than the inner diameter of the sheath 1002 so that the tip 1006 cannot be drawn into sheath 1002 as the sheath and tip are moved relative to one another. The distal end of the tip 1006 preferably has a smoothly curved tapered surface to facilitate the forward movement of delivery catheter assembly 1000 through the arterial system. The tip 1006 has a bore (not shown) that enables a first guide wire 1007 (and possibly medication, dye and the like) to exit from delivery catheter assembly 1000.

An arteriotomy is initially performed on a leg and, under conventional fluoroscopic guidance techniques, the first guide wire 1007 is introduced through the femoral artery of the leg (not shown) and iliac artery (e.g., right iliac artery 906 in the example shown (FIG. 10L)) into the aorta 900. The first guide wire 1007 guides the delivery catheter assembly 100 through these arteries during delivery.

Figure 10A:
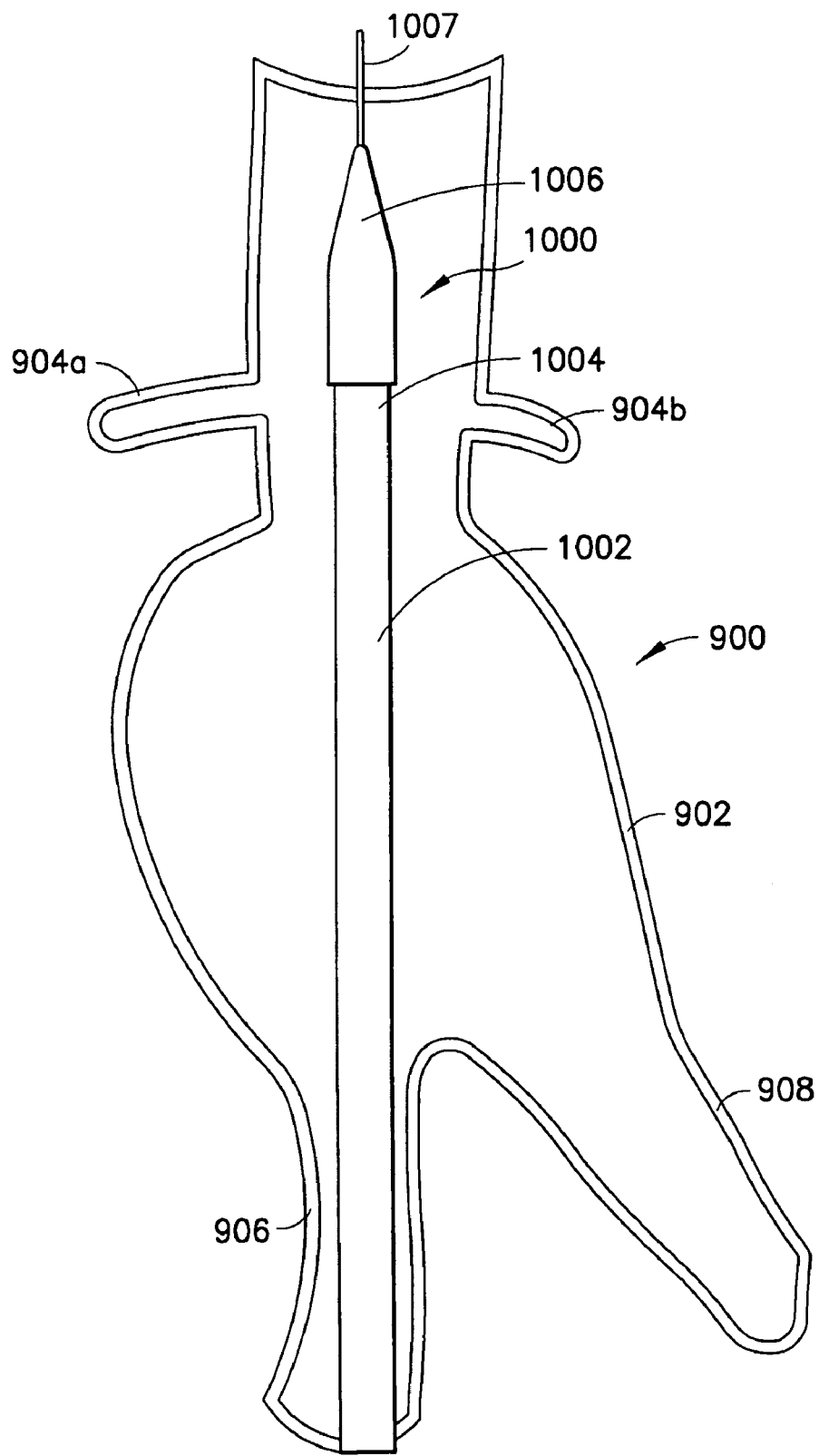
FIGS. 10A-10O are pictorial illustrations of catheter-based delivery mechanisms and associated surgical procedures for the repair of an abdominal aortic aneurysm with the modular stent graph system of FIG. 1.
Figure 10B:
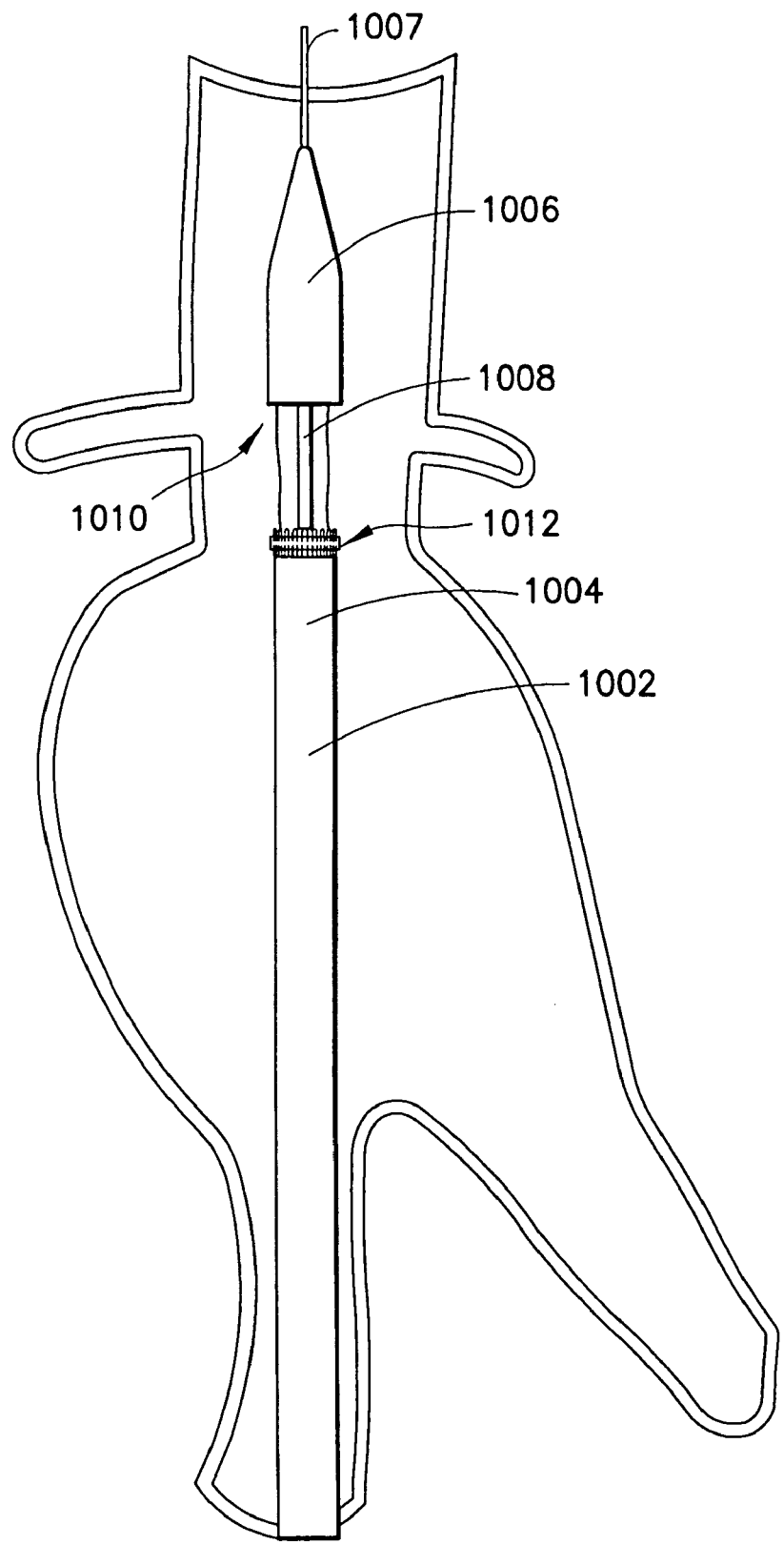

As shown in FIG. 10B, an inner tubular member (or mandrel) 1008 is arranged in the sheath 1002 and connected at is distal end to the tip 1006 for slidable longitudinal movement of the tip 1006 relative to the sheath 1002. Typical materials for forming the member 1008 include biocompatible polymers, for example, nylon, TEFLON, polytetrafluoroethylene, polyethylene and the like. Biocompatible metals can also be used. At its proximal end (not shown), the member 1008 may be fitted with any number of conventional accessories, such as a hand grip (and/or a Y-connector, hemostasis valve, or stopcock).

The proximal end of the tip 1008 defines a interior cavity 1010 that holds the fixation ring 203 of the primary stent 110 in its collapsed condition, while the distal end 1004 of the sheath 1002 defines an interior cavity 1012 that holds the graft-support segments 207a, 207b, 207c, 207d and the leg support segment 213 of the primary stent 110 as well as the primary graft 112 and the seal 117 all in their collapsed condition.

As shown in FIGS. 10A and 10B, the catheter assembly 1000 is positioned such that the distal end 1104 of the sheath 1002 is disposed below the renal arteries 904A, 904B adjacent healthy tissue (e.g., adjacent the infrarenal neck).

Figure 10C:
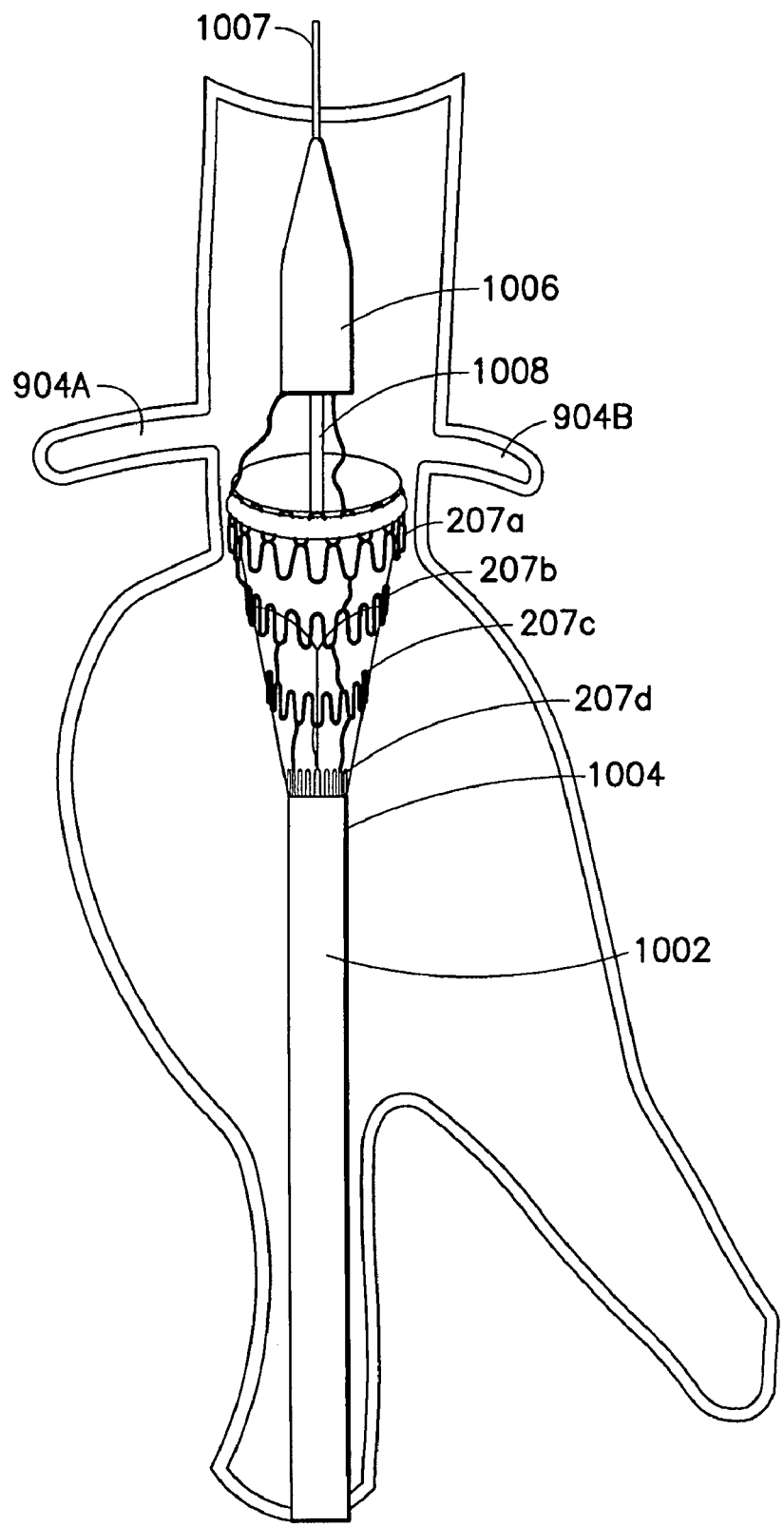

As shown in FIG. 10C, with the inner member 1008 held in a fixed longitudinal position (and thus the tip 1008 held in a fixed longitudinal position), the sheath 1002 is retracted proximally to deploy from the cavity 1010 the graft-support segments 207a (and possibly the segments 207b, 207c, 207d, 213) as well as corresponding portions of the primary graft 112 and the seal 117. In this manner the seal 117 and the graft support segment 207a are positioned adjacent the infrarenal neck as shown.

Figure 10D:
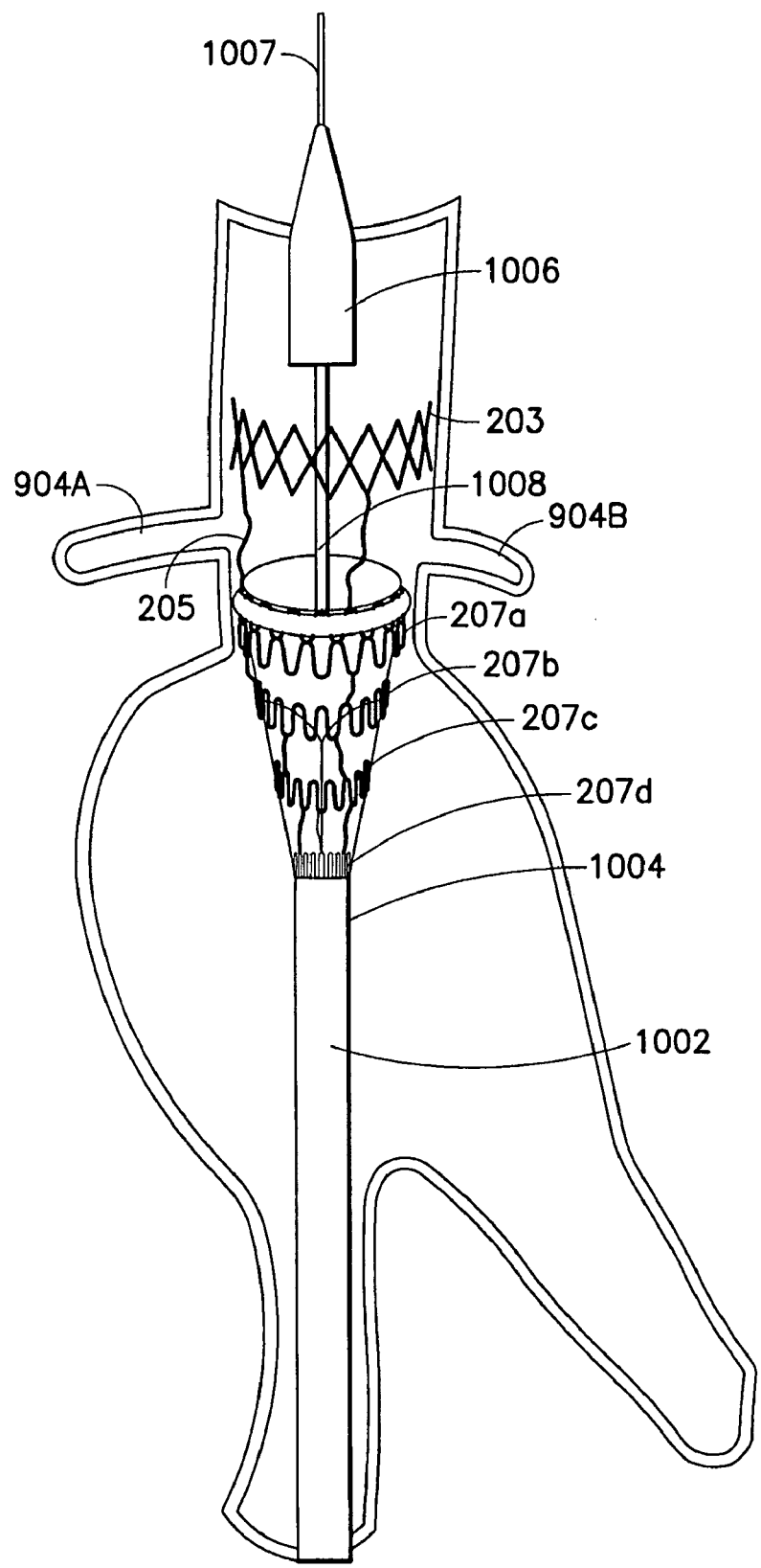

As shown in FIG. 10D, with the sheath 1002 held in a fixed longitudinal position, the inner member 1008 (and thus the tip 1008 connected thereto) is moved distally to deploy from the cavity 1010 the fixation ring 203 of the primary stent 110. In its expanded state, the fixation ring 203 contacts the inner wall of aorta above the renal arteries 904A, 904B (i.e., supra-renal fixation) in order to prevent the primary stent 100 from moving distally and proximally in the aorta as described above. The openings afforded by the diamond shaped elements of the fixation ring 103 allow for tissue ingrowth and permanent fixation. The suspenders 205 connect the graft-supporting stent elements to the fixation ring 203 without blocking blood flow to the renal arteries 904A, 904B. The flexibility of the suspenders 205 (which is primarily dictated by the corrugated design of the suspenders) allows for the primary stent to lengthen and change shape in the event that the morphology of aneurysm changes over time, thereby aiding in improved fixation in such cases.

Figure 10E:
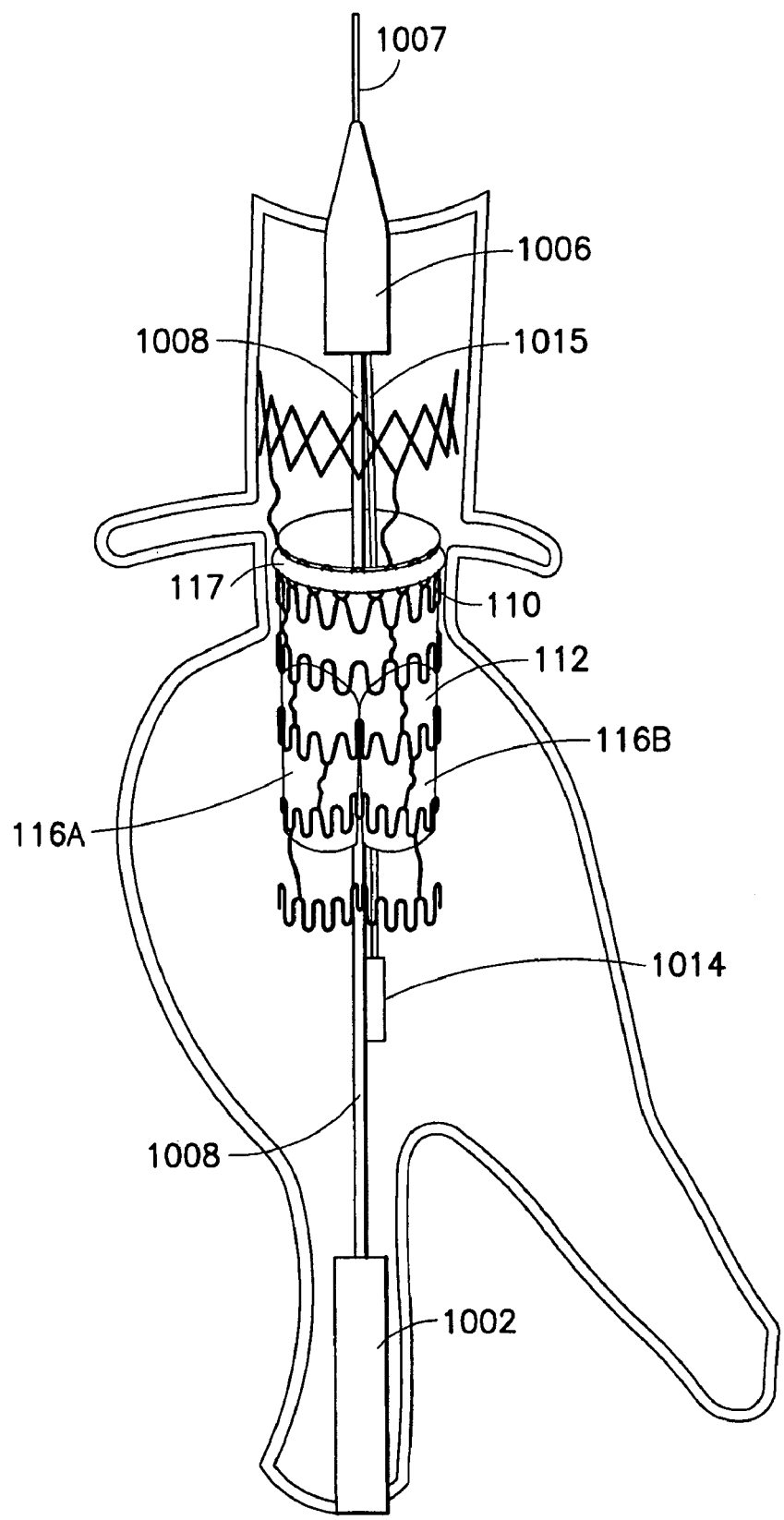

As shown in FIG. 10E, with the inner member 1008 held in a fixed longitudinal position (and thus the tip 1008 held in a fixed longitudinal position), the sheath 1002 is retracted proximally to deploy from the cavity 1010 the remaining graft-support segments (such as segments 207d, 213) as well as corresponding portions of the primary graft 112. In this manner the seal 1007, the primary stent 110, and the primary graft 112 are positioned at the aneurysm site as shown. A biocompatible magnet 1014 (which is preferably realized from neodymium boron) is affixed to the end of a second guide wire 1015 that extends through one of the pants (in the example shown, pant 116B). The first guide wire 1007 and the delivery catheter system 100 extend through the other pant leg (in the example shown, pant leg 116A (FIG. 10L)).

Figure 10F:
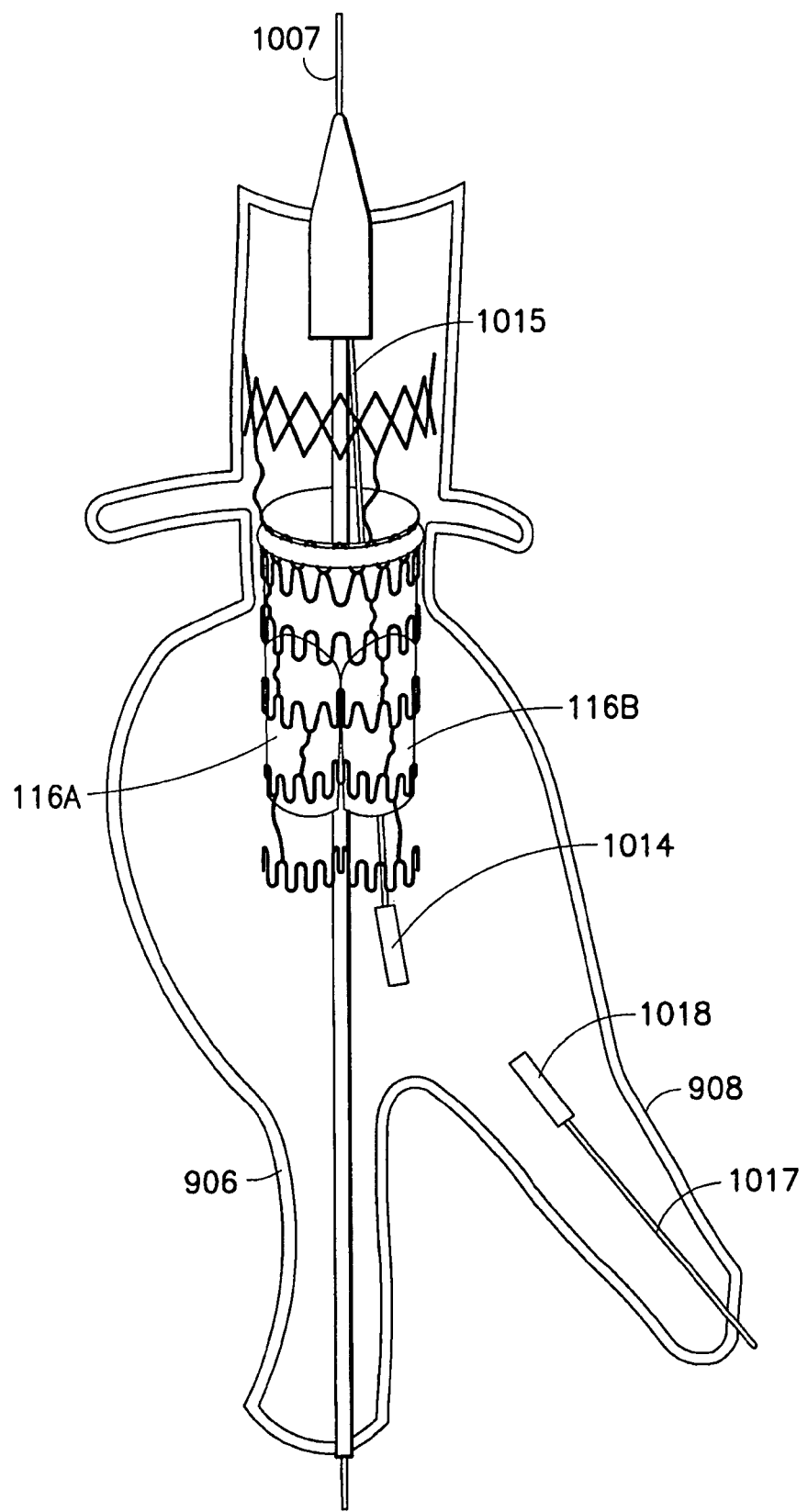
Figure 10G:
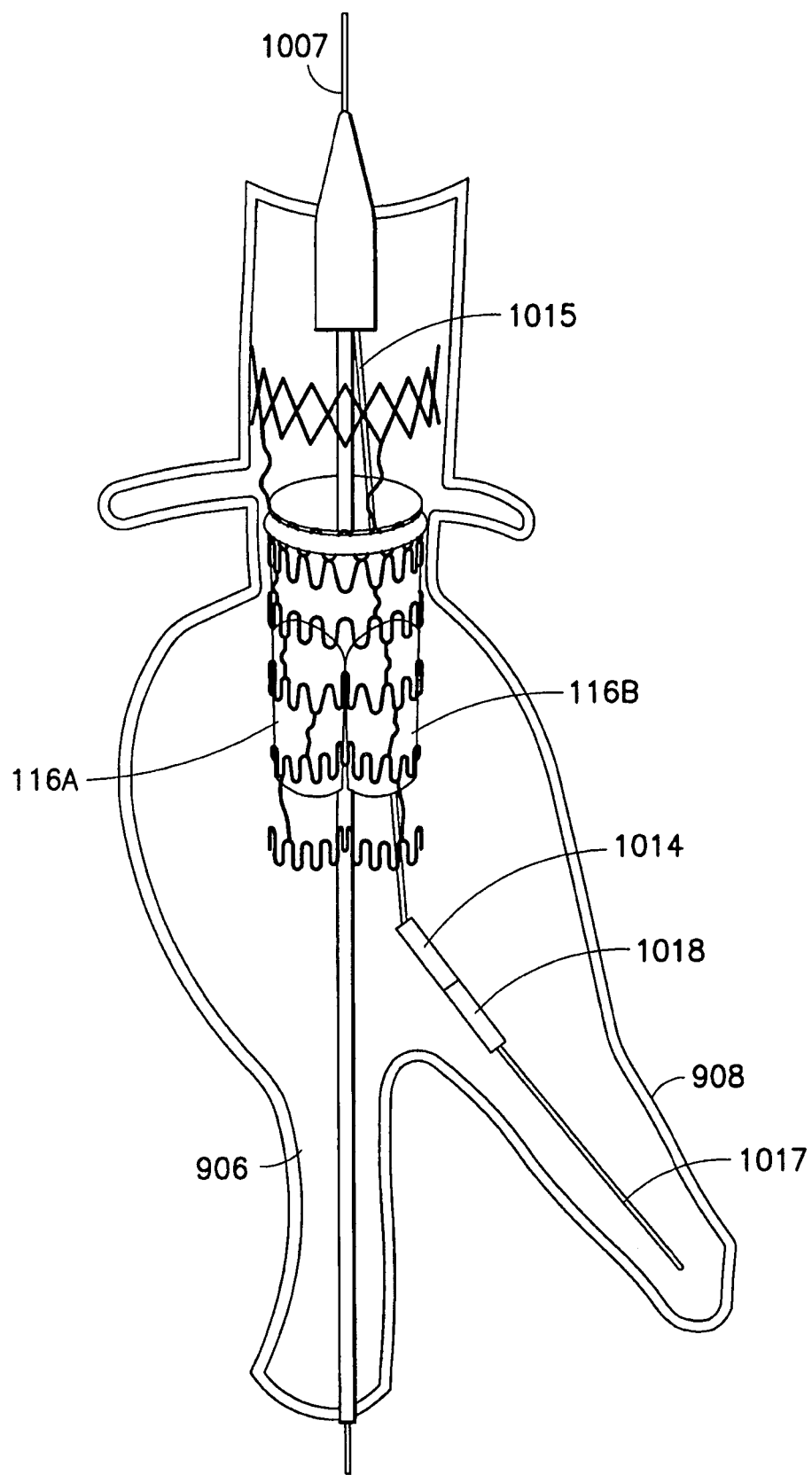
Figure 10H:
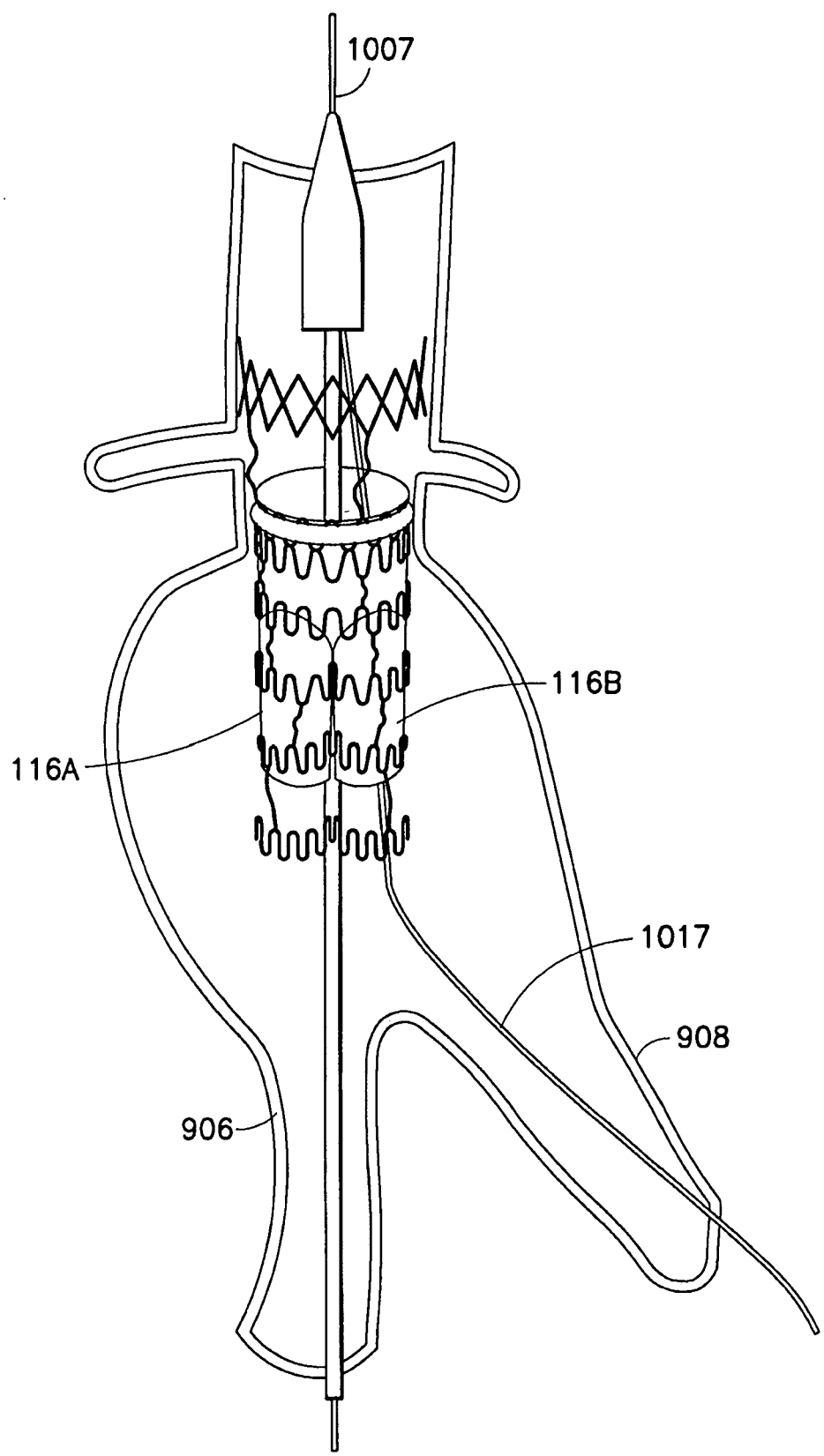

As shown in FIGS. 10F-10H, a third guide wire 1017 with a biocompatible magnet 1018 (which is preferably realized from neodymium boron) affixed to its distal end is inserted into the iliac artery that is not traversed by the first guide wire 1007 (in this example the left iliac artery 908). The attraction between the magnets 1014 and 1018 is used to couple the third guide wire 1017 to the second guide wire 1015. The second guide wire is then repositioned to pull the third guide wire 1017 through the pant (e.g., pant 116B) traversed by the third guide wire (FIG. 10H).

Figure 10I:
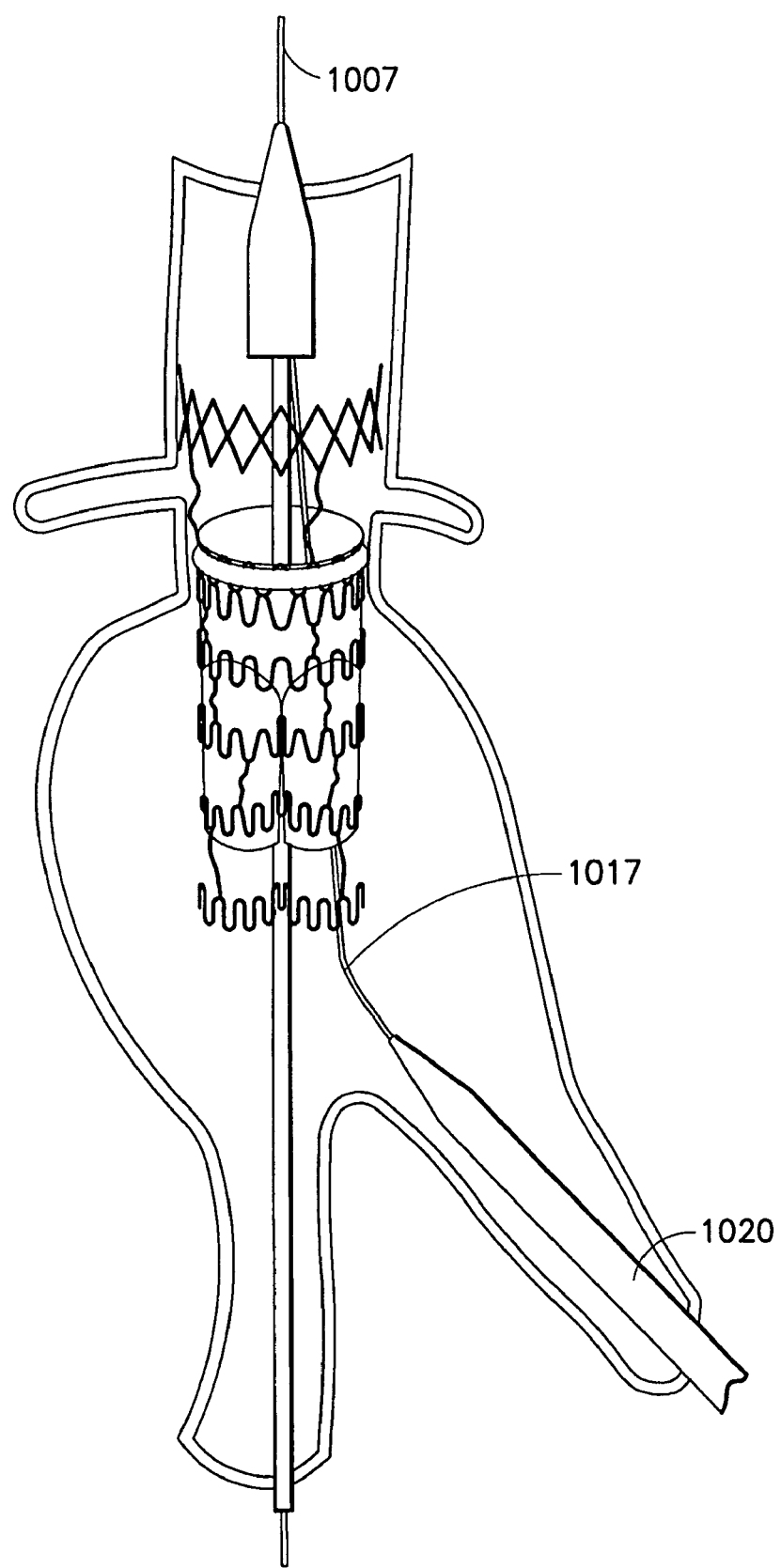
Figure 10J:
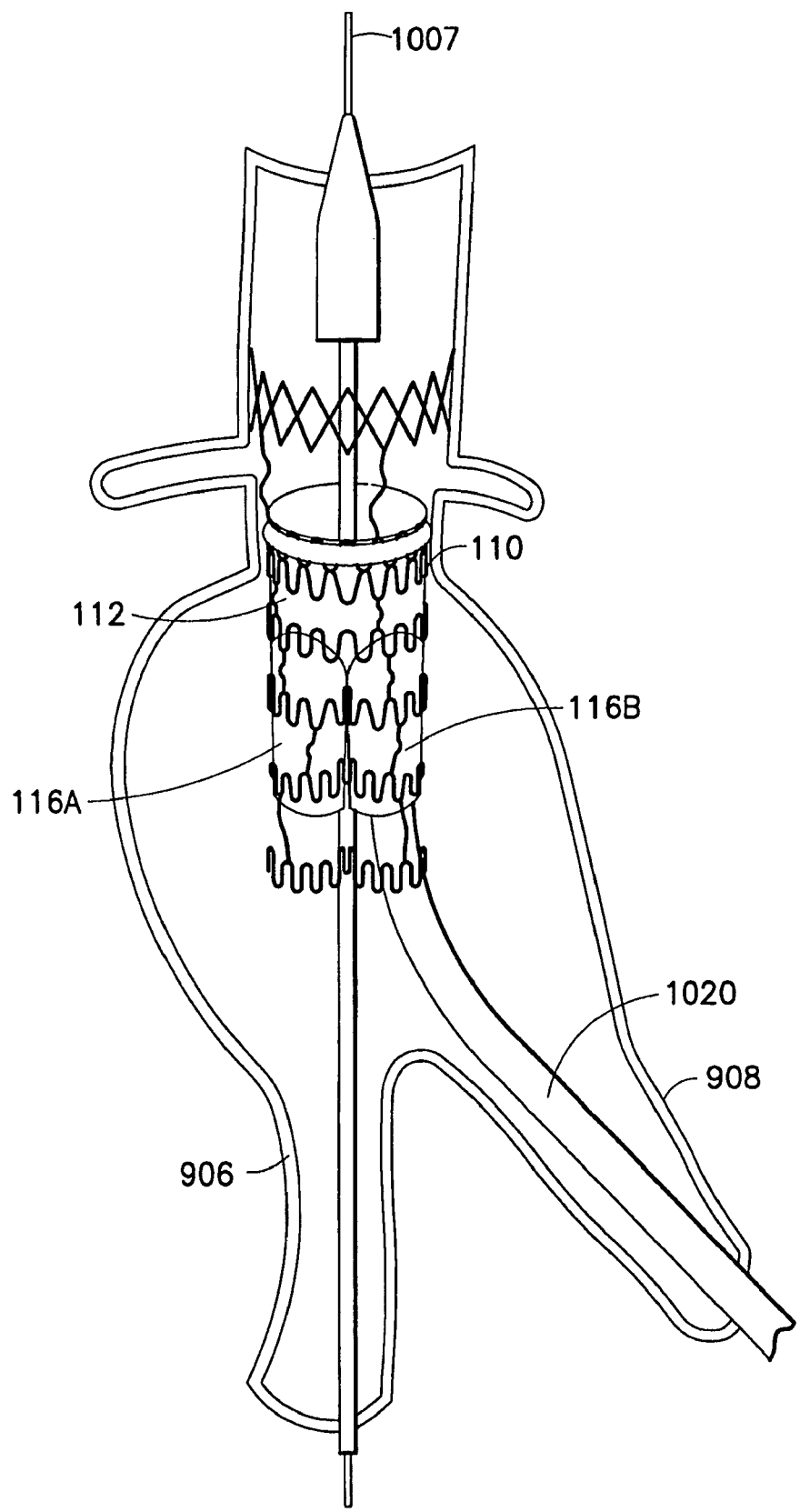
Figure 10K:
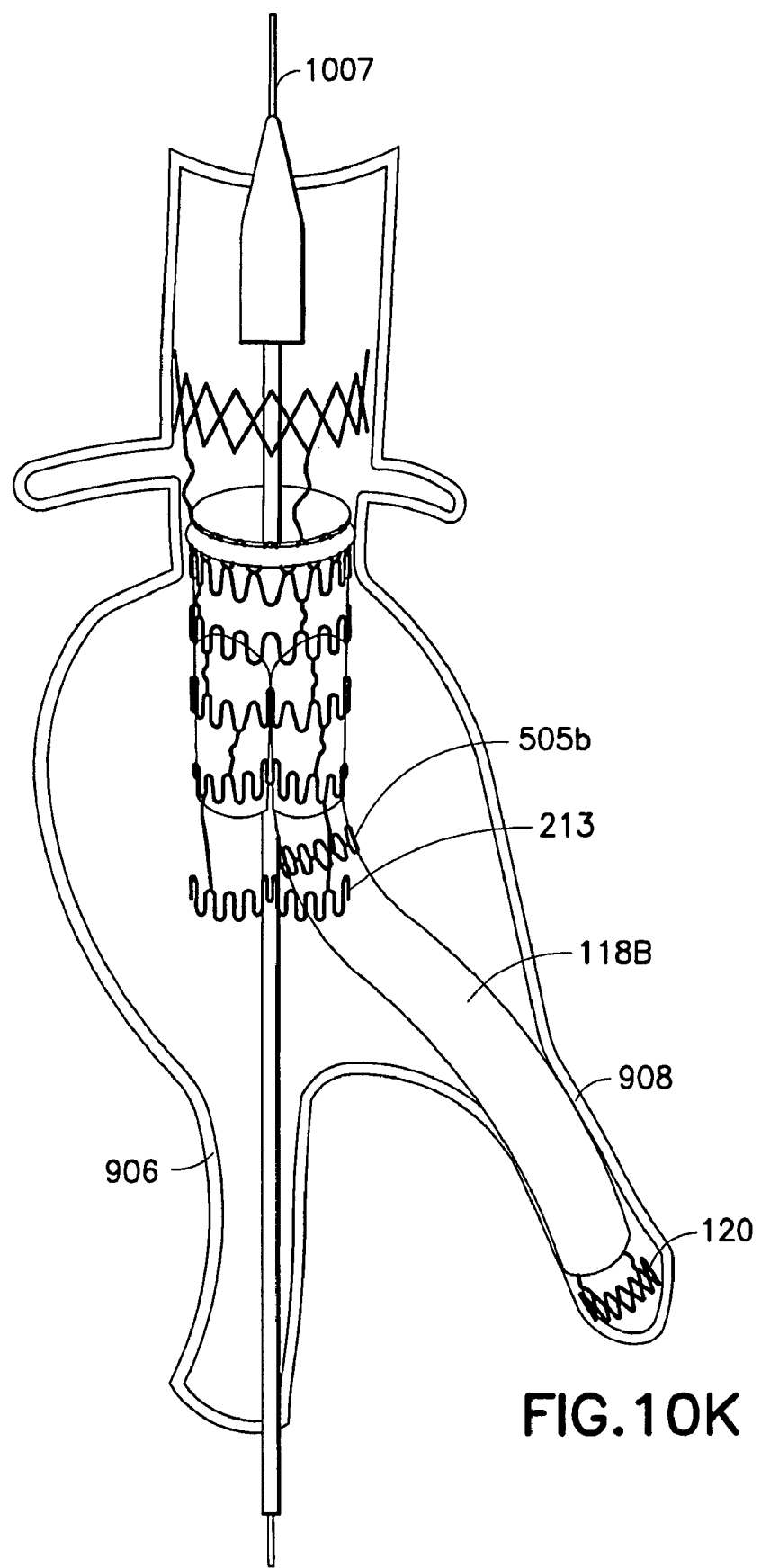

As shown in FIGS. 10I-10K, a second flexible delivery catheter assembly 1020, which is similar in construction to the delivery catheter assembly 1000, is extended along the third guide wire 1017 through the iliac artery (e.g., the left iliac artery 908) traversed by the third guide wire 1017 (FIG. 10I). The second delivery catheter assembly 1020 holds a leg graft (e.g., leg graft 118B) that is to be interconnected to the pant (e.g., pant 116B) traversed by the third guide wire. This leg graft is held in the second delivery catheter assembly 1020 in its compressed state. The tip of the second flexible delivery catheter 1020 is positioned inside this pant (e.g., pant 116B in FIG. 10J) and the second delivery catheter system 1020 is manipulated (similar to the operations described above for deployment of the primary stent 110, primary graft 112 and seal 117) to deploy the distal end of the leg graft inside the respective pant (together with the stent component 505b interlocking with the segment 213 of the primary stent 110). The proximal end of the leg graft is deployed within the respective iliac artery, where it is actively fixated thereto by the stent 120 (FIG. 10K).

Figure 10L:
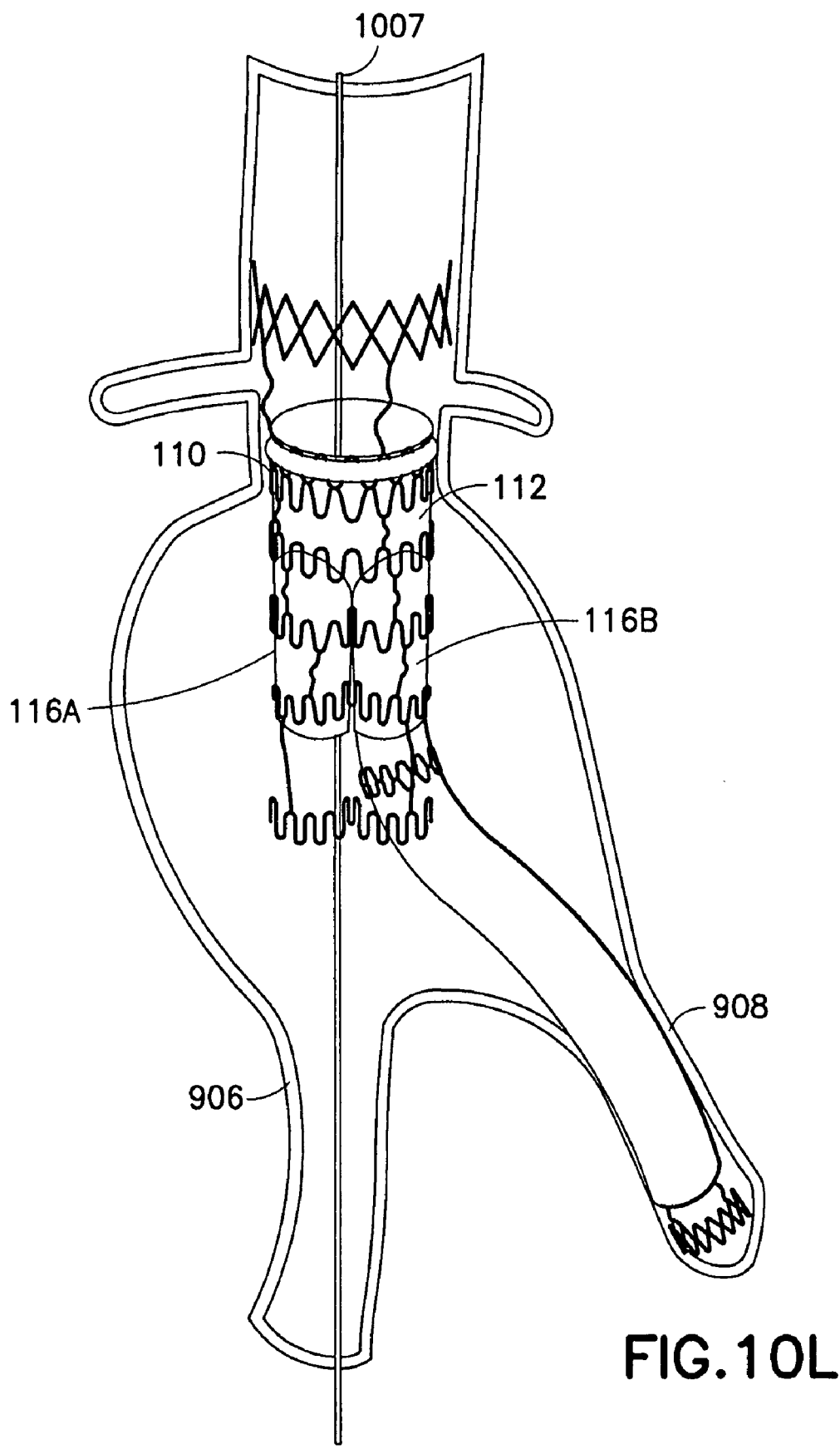

As shown in FIG. 10L, the second delivery catheter assembly 1020 as well as the primary delivery catheter assembly 1000 are withdrawn from the arterial system, leaving the first guide wire 1007, which passes through the unconnected pant (e.g., pant 116A) of the primary graft 112.

Figure 10M:
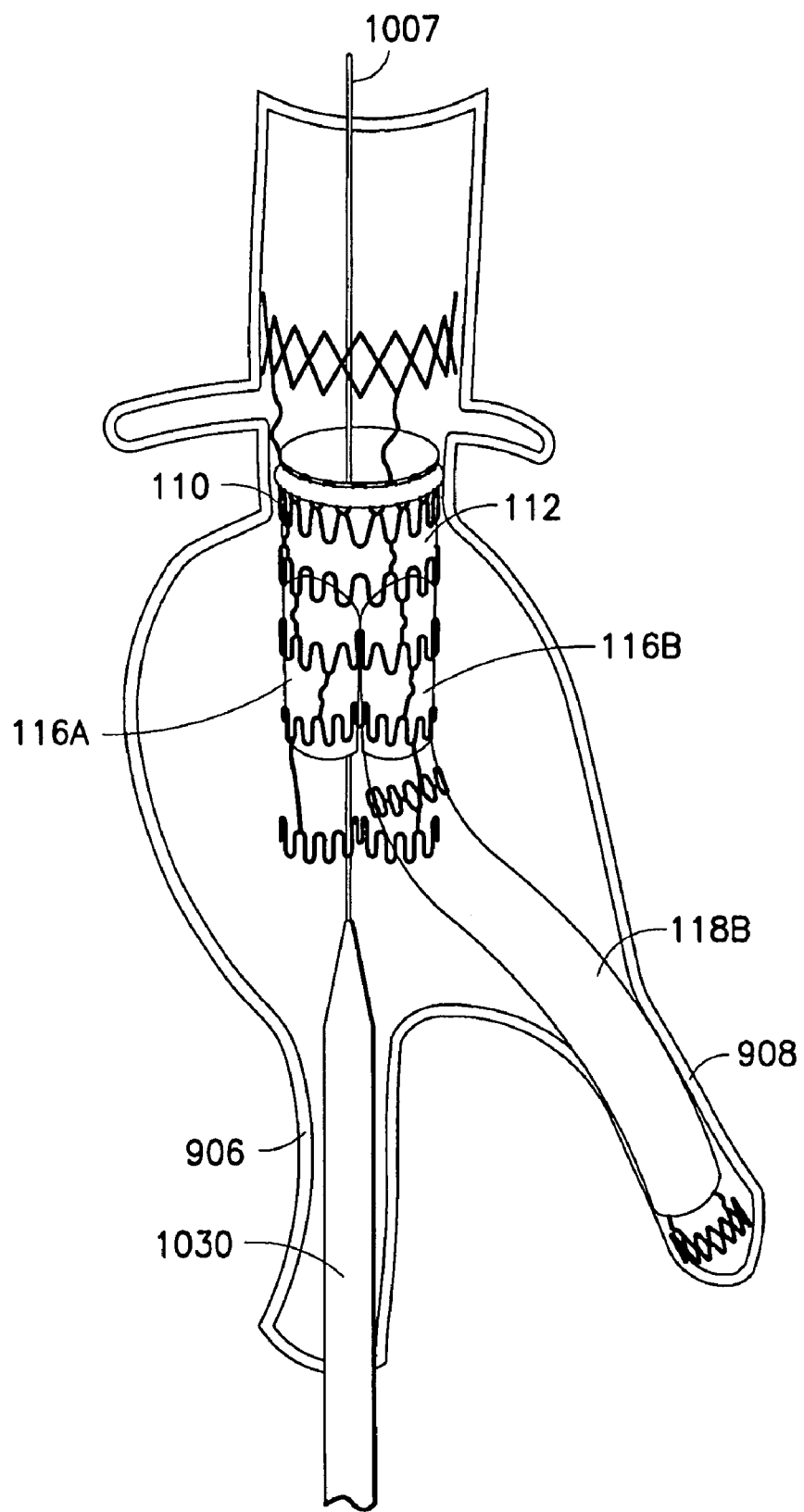
Figure 10N:
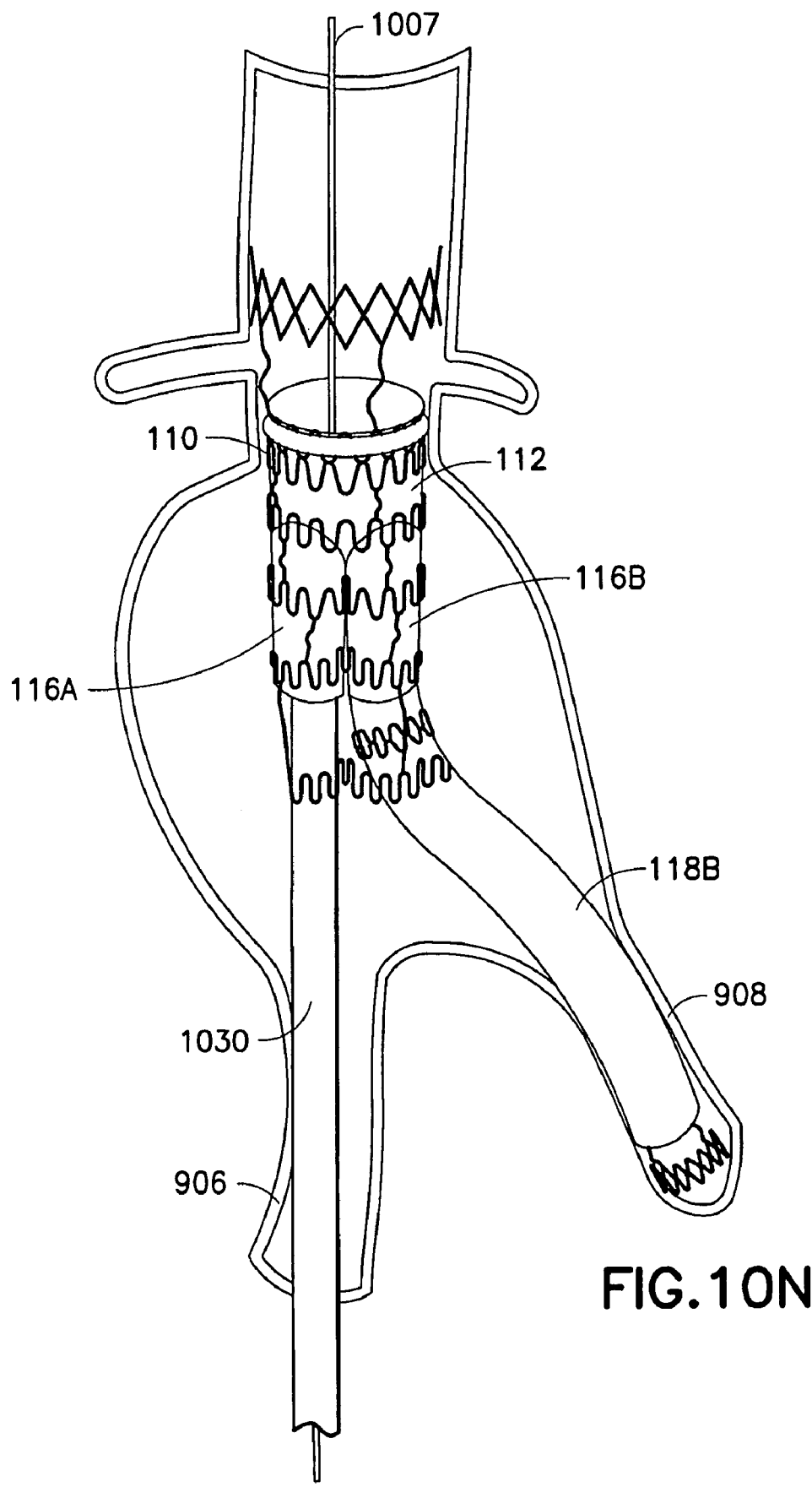
Figure 100:
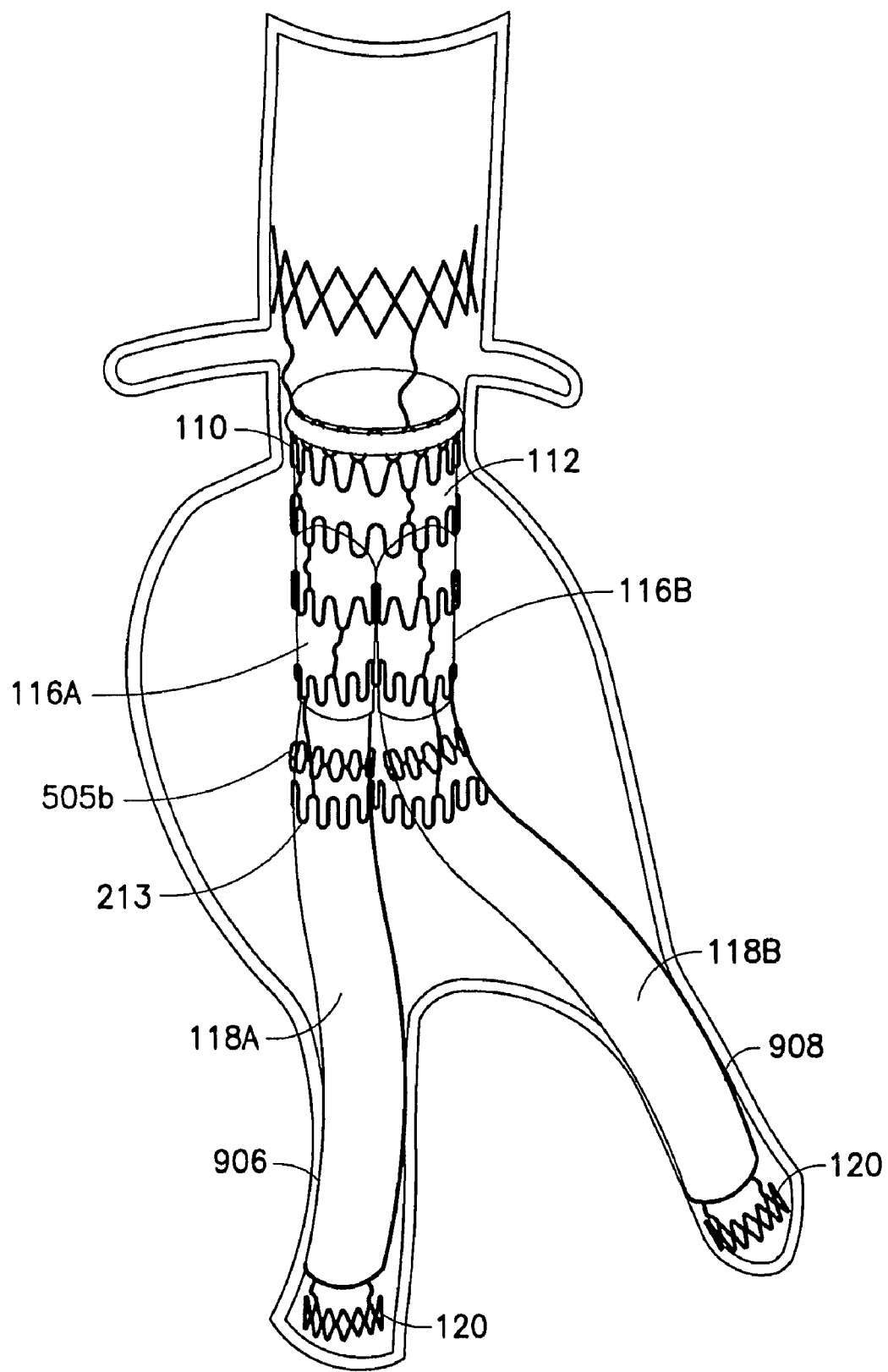

As shown in FIGS. 10M-10O, a third flexible delivery catheter assembly 1030, which is similar in construction to the second delivery catheter assembly 1020 or possibly is the same assembly, is extended along the first guide wire 1007 through the iliac artery (e.g., the right iliac artery 906) traversed by the first guide wire 1007 (FIG. 10M). The third delivery catheter assembly 1030 holds a leg graft (e.g., leg graft 118A) that is to be interconnected to the pant (e.g., pant 116A) traversed by the first guide wire. This leg graft is held in the third delivery catheter assembly 1030 in its compressed state. The tip of the third flexible delivery catheter 1030 is positioned inside this pant (e.g., pant 116A in FIG. 10N) and the third delivery catheter system 1030 is manipulated (similar to the operations described above for deployment of the primary stent 110, primary graft 112 and seal 117) to deploy the distal end of the leg graft inside the respective pant (together with the stent component 505a interlocking with the segment 213 of the primary stent 110). The proximal end of the leg graft is deployed within the respective iliac artery, where it is actively fixated thereto by the stent 120 (FIG. 10O).

Finally, the third delivery catheter assembly 1030 as well as the guide wire 1007 are withdrawn from the patient (FIG. 10O), and the arteriotomies sutured.

Once deployed and assembled together according to the foregoing procedure, the components of modular stent graft system 100 form a bifurcated graft which is fully self supporting. That is, as a result of its bottom-up assembly, the biomechanical forces exerted on the graft, particularly from the flow of blood, are supported along its entire length in a columnar fashion.

It will be appreciated, of course, that variations in the foregoing procedure can be made without departing from the scope of the present invention. For example, rather than relying merely upon the outward radial forces exerted by the expanding stent structures 110, 120, 122, the appropriate ends of these components may be provided with mechanical structures, such as barbs, sutures and the like, to assure that the components are securely held together.

The modular stent graft system and surgical methods of the present invention overcome many of the difficulties associated with delivering and securing the bifurcated grafts of the prior art. By providing a stent graft in the form of modular components that can be individually selected and assembled together, the present invention permits more accurate sizing of the components to the individual patient. Moreover, the stent graft preferably employs a laser cut stent from nitinol (or other shape memory metal), which eliminates metal to metal wear at stress points. It also preferably employs a polymeric based adhesive (or filler) that binds the supporting stent to the bifurcated graft. This feature eliminates reliance on sutures and allows pull down. Moreover, the polymeric base adhesive couples motion of the bifurcated graft with the motion of the stent to prevent abrasion. The stent graft also employs active fixation to the aorta wall above the renal arteries (e.g., suprarenal fixation) together with barbs that designed to prevent perforation of aorta. The flexible suspenders of the stent prevent jailing of renal arteries and together with the suprarenal fixation can accommodate aneurysms with infrarenal necks that are less than 5 mm in length. The flexibility of the suspenders of the stent allow for bendability, which can be up to 45 degrees in the renal area and up to 60-90 degrees below the renal area. These features allow the stent graft to accommodate tortuous aneurysms. Moreover, the stent and leg grafts incorporate an improved stent-based locking mechanism to prevent disarticulation of the legs from the bifurcated graft. Moreover, the leg grafts preferably employ a stretchable and compressible polymeric tube-in-tube structure with universal bendability, which accommodate morphing aneurysms. The stent graft system and the delivery catheter assemblies described herein also provide for precise and controllable placement in the aorta. In addition, the stent graft system is simple and inexpensive to manufacture (e.g., not labor intensive).

There have been described and illustrated herein a modular stent graft system and surgical methods for repairing an abdominal aortic aneurysm using such stent graft system. While particular embodiments of the invention have been described, it is not intended that the invention be limited thereto, as it is intended that the invention be as broad in scope as the art will allow and that the specification be read likewise. Thus, while particular geometries, shapes and configurations have been disclosed for the elements of the stent component, it will be appreciated that other geometries, shapes and configurations can be used as well. Similarly, while particular geometries, shapes and configurations have been disclosed for the elements of the primary graft component and the leg graft extensions, it will be appreciated that other geometries, shapes and configurations can be used as well. In addition, while particular types of materials and methods of manufacture have been disclosed, it will be understood that other types of materials and methods of manufacture can be used. Moreover, while particular catheter-based delivery mechanisms and techniques have been disclosed for deploying the stent graft in the aorta, it will be appreciated that other mechanisms and techniques could be used as well. In addition, the catheter-based delivery mechanisms and techniques for deploying the stent graft in the human aorta as disclosed herein can be used for deployment in non-human mammals and human cadavers for testing purposes. It will therefore be appreciated by those skilled in the art that yet other modifications could be made to the provided invention without deviating from its spirit and scope as claimed.

We claim:

1. A modular stent graft for repairing an aneurysm in the human aorta, the stent graft comprising:
   a collapsible flexible bifurcated graft having a bifurcated hip section, a first pant leg section that extends from said bifurcated hip section to a first proximal end, and a second pant leg section that extends from said bifurcated hip section to a second proximal end;
   at least one collapsible stent member including stent elements that surround and support the bifurcated graft, a first set of stent elements that are proximally disposed relative to and spaced apart from said first proximal end of said first pant leg section by at least one connector element, and a second set of stent elements that are proximally disposed relative to and spaced apart from said second proximal end of said second pant leg section by at least one connector element;
   a collapsible flexible first leg graft that interconnects to said first pant leg section of said bifurcated graft, said first leg graft having an exterior surface;
   a collapsible flexible second leg graft that interconnects to said second pant leg section of said bifurcated graft, said second leg graft having an exterior surface;
   a third set of stent elements that are disposed external to and surrounding said exterior surface of said first leg graft at a position offset proximally from the distal end of said first leg graft, wherein said third set of stent elements are operably disposed between said first proximal end of said first pant leg section and said first set of stent elements to thereby maintain interconnection between said first leg graft and said first pant leg section of said bifurcated graft; and
   a fourth set of stent elements that are disposed external to and surrounding said exterior surface of said second leg graft at a position offset proximally from the distal end of said second leg graft, wherein said fourth set of stent elements are operably disposed between said second proximal end of said second pant leg section and said second set of stent elements to thereby maintain interconnection between said second leg graft and said second pant leg section of said bifurcated graft.

2. A modular stent graft according to claim 1, wherein:
   said third set of stent elements interlock to said first set of stent elements for securely connecting said first leg graft to said first pant leg section of said bifurcated graft; and
   said fourth set of stent elements interlock to said second set of stent elements for securely connecting said second leg graft to said second pant leg section of said bifurcated graft.

3. A modular stent graft according to claim 1, wherein:
   said third set of stent elements are deployed in a position distally relative to said first set of stent elements by passing said third set of stent elements in a collapsed state through said first set of stent elements in an expanded state; and
   said fourth set of stent elements are deployed in a position distally relative to said second set of stent elements by passing said fourth set of stent elements in a collapsed state through said second set of stent elements in an expanded state.

4. A modular stent graft according to claim 1, further comprising:
   a fifth set of stent elements that are disposed adjacent to a distal portion of said first leg graft, said distal portion of said first leg graft operably disposed within said first pant leg section of said bifurcated graft, wherein in an expanded state said fifth set of stent elements interconnect said first leg graft to said first pant leg section; and
   a sixth set of stent elements that are disposed adjacent to a distal portion of said second leg graft, said distal portion of said second leg graft operably disposed within said second pant leg section of said bifurcated graft, wherein in an expanded state said sixth set of stent elements interconnect said second leg graft to said second pant leg section.

5. A modular stent graft according to claim 4, further comprising:
longitudinal stent elements that are disposed external to said exterior surface of said first leg graft and that extend between said third set of stent elements and said fifth set of stent elements; and
longitudinal stent elements that are disposed external to said exterior surface of said second leg graft and that extend between said fourth set of stent elements and said sixth set of stent elements.

6. A modular stent graft according to claim 1, wherein:
said at least one collapsible stent member includes a ring of stent elements that is disposed distally relative to a distal end of said bifurcated graft element, said ring of stent elements for supporting said bifurcated graft element in the aorta.

7. A modular stent graft according to claim 6, wherein:
said ring of stent elements is operably disposed above the renal arteries of the aorta.

8. A modular stent graft according to claim 6, further comprising:
flexible longitudinal stent elements that extend distally from the distal end of said bifurcated graft element to said ring of stent elements.

9. A modular stent graft according to claim 8, wherein:
said longitudinal stent elements are adapted such that they do not substantially block blood flow to the renal arteries of the aorta.

10. A modular stent graft according to claim 8, wherein:
said longitudinal stent elements are corrugated to provide bendability.

11. A modular stent graft according to claim 6, wherein:
said ring of stent elements has two sets of strut elements that are disposed at an angle relative to one another to define acute junctions therebetween and, in an expanded state, extend at opposite directions relative to the central axis of said ring of stent elements for fixation to the inner wall of the vessel lumen, wherein one of said directions prevents the stent graft from moving distally in the aorta, and the other of said directions prevents the stent graft from moving proximally in the aorta.

12. A modular stent graft according to claim 11, wherein:
said ring of stent elements has laser cut barbs that project from the acute junctions.

13. A modular stent graft according to claim 6, wherein:
said ring of stent elements has open spaces that allows for tissue ingrowth and permanent fixation over time.

14. A modular stent graft according to claim 1, further comprising:
a seal surrounding a distal end of said bifurcated graft.

15. A modular stent graft according to claim 14, wherein:
said seal is porous foam.

16. A modular stent graft according to claim 14, wherein:
said seal is loaded with a therapeutic drug that is released over time.

17. A modular stent graft according to claim 1, further comprising:
a polymeric material that bonds said at least one collapsible stent member to said bifurcated graft.

18. A modular stent graft according to claim 17, wherein:
said polymeric material comprises a polyisobutylene-based material capped with a glassy segment.

19. A modular stent graft according to claim 18, wherein:
said polymeric material comprises SIBS.

20. A modular stent graft according to claim 1, wherein:
said first and second leg grafts each comprise a flexible and compressible polymeric tube-in-tube structure.

21. A modular stent graft according to claim 20, wherein:
said tube-in-tube-structure can pull down to provide at least a 20 percent increase in length.

22. A modular stent graft according to claim 21, wherein:
said tube-in-tube structure comprises an outer polymeric tube bound to an inner polymeric tube by a polymeric material.

23. A modular stent graft according to claim 22, wherein:
said inner tube is realized from a flexible biocompatible material that allows for pull down such that the length and diameter of said inner tube changes in response to axial forces applied to the ends of said inner tube.

24. A modular stent graft according to claim 22, wherein:
said inner tube is realized from a knitted or braided fabric with a pore size and density that prohibits blood flow therethrough.

25. A modular stent graft according to claim 22, wherein:
the outer tube is realized from a biocompatible polymeric material braided with Wallsten-type pattern that allows for pull down such that the length and diameter of the outer tube changes in response to axial forces applied to the ends of the outer tube.

26. A modular stent graft according to claim 22, wherein:
said polymeric material comprises a polyisobutylene-based material capped with a glassy segment.

27. A modular stent graft according to claim 26, wherein:
said polymeric material comprises SIBS.

28. An intraluminal stent graft comprising:
a collapsible flexible bifurcated graft having a bifurcated hip section, a first pant leg section that extends from said bifurcated hip section to a first proximal end, and a second pant leg section that extends from said bifurcated hip section to a second proximal end;
a collapsible unitary first stent member including stent elements that surround and support said bifurcated graft, a first set of stent elements that are disposed distally from a distal end of said bifurcated graft for supporting said bifurcated graft in the aorta, a second set of stent elements that are proximally disposed relative to and spaced apart from said first proximal end of said first pant leg section by at least one connector element, and a third set of stent elements that are proximally disposed relative to and spaced apart from said second proximal end of said second pant leg section by at least one connector element; and
a collapsible flexible first leg graft having a second stent member with a fourth set of stent elements coupled thereto;
a collapsible flexible second leg graft having a third stent member with a fifth set of stent elements coupled thereto;
wherein said fourth set of stent elements are disposed external to and surrounding an exterior surface of said first leg graft and are operably disposed proximal to said first proximal end of said first pant leg section and distally adjacent to said second set of stent elements in order to maintain interconnection between said first leg graft to said first pant leg section of said bifurcated graft; and
wherein said fifth set of stent elements are disposed external to and surrounding an exterior surface of said second leg graft and are operably disposed proximal to said second proximal end of said second pant leg section and distally adjacent to said third set of stent elements in order to maintain interconnection between said second leg graft to said second pant leg section of said bifurcated graft.

29. An intraluminal stent graft according to claim 28, wherein:
said fourth set of stent elements are deployed in a position distally relative to said second set of stent elements by passing said fourth set of stent elements in a collapsed state through said second set of stent elements in an expanded state; and
said fifth set of stent elements are deployed in a position distally relative to said third set of stent elements by passing said fifth set of stent elements in a collapsed state through said third set of stent elements in an expanded state.

30. An intraluminal stent graft according to claim 28, further comprising:
flexible longitudinal stent elements that extend distally from the distal end of said bifurcated graft to said first set of stent elements.

31. An intraluminal stent graft according to claim 30, wherein:
said longitudinal stent elements are adapted such that they do not substantially block blood flow to the renal arteries of the aorta.

32. An intraluminal stent graft according to claim 30, wherein:
said longitudinal stent elements are corrugated to provide bendability.

33. An intraluminal stent graft according to claim 28, wherein:
said first set of stent elements have two sets of strut elements that are disposed at an angle relative to one another to define acute junctions therebetween and, in an expanded state, extend at opposite directions relative to the central axis of said strut elements for fixation to the inner wall of the vessel lumen, wherein one of said directions prevents the stent graft from moving distally in the aorta, and the other of said directions prevents the stent graft from moving proximally in the aorta.

34. An intraluminal stent graft according to claim 33, wherein:
said first set of stent elements has laser cut barbs that project from the acute junctions.

35. An intraluminal stent graft according to claim 33, wherein:
said first set of stent elements has open spaces that allows for tissue ingrowth and permanent fixation over time.

36. An intraluminal stent graft according to claim 28, further comprising:
a seal surrounding a distal end of said bifurcated graft.

37. An intraluminal stent graft according to claim 36, wherein:
said seal is porous foam.

38. An intraluminal stent graft according to claim 36, wherein:
said seal is loaded with a therapeutic drug that is released over time.

39. An intraluminal stent graft according to claim 28, further comprising:
polymeric material that binds said collapsible unitary first stent member to said bifurcated graft.

40. An intraluminal stent graft according to claim 39, wherein:
said polymeric material comprises a polyisobutylene-based material capped with a glassy segment.

41. An intraluminal stent graft according to claim 40, wherein:
said polymeric material comprises SIBS.

42. An intraluminal stent graft according to claim 28, wherein:
said first and second leg grafts each comprise a flexible and compressible polymeric tube-in-tube structure.

43. An intraluminal stent graft according to claim 42, wherein:
said tube-in-tube-structure can pull down to provide at least a 20 percent increase in length.

44. An intraluminal stent graft according to claim 42, wherein:
said tube-in-tube structure comprises an outer polymeric tube bound to an inner polymeric tube by a polymeric material.

45. An intraluminal stent graft according to claim 44, wherein:
said inner tube is realized from a flexible biocompatible material that allows for pull down such that the length and diameter of said inner tube changes in response to axial forces applied to the ends of said inner tube.

46. An intraluminal stent graft according to claim 44, wherein:
said inner tube is realized from a knitted or braided fabric with a pore size and density that prohibits blood flow therethrough.

47. An intraluminal stent graft according to claim 44, wherein:
the outer tube is realized from a biocompatible polymeric material braided with Wallsten-type pattern that allows for pull down such that the length and diameter of the outer tube changes in response to axial forces applied to the ends of the outer tube.

48. An intraluminal stent graft according to claim 44, wherein:
said polymeric material comprises a polyisobutylene-based material capped with a glassy segment.

49. An intraluminal stent graft according to claim 48, wherein:
said polymeric material comprises SIBS.

50. A modular stent graft for repairing an aneurysm in the human aorta, the stent graft comprising:
a collapsible flexible bifurcated graft having a pant leg section extending to a proximal end;
at least one collapsible stent member including a first set of stent elements that surround and support the bifurcated graft and a second set of stent elements that are proximally disposed relative to and spaced apart from said proximal end of said pant leg section by at least one connector element;
a collapsible flexible leg graft that interconnects to said pant leg section of said bifurcated graft, said leg graft having an exterior surface;
a third set of stent elements that are disposed external to and surrounding said exterior surface of said leg graft at a position offset proximally from the distal end of said leg graft, wherein said third set of stent elements are operably disposed between said proximal end of said pant leg section and said second set of stent elements to thereby maintain interconnection between said leg graft and said pant leg section of said bifurcated graft.

51. A modular stent graft according to claim 50, wherein:
said third set of stent elements interlock to said second set of stent elements for securely connecting said leg graft to said pant leg section of said bifurcated graft.

52. A modular stent graft according to claim 50, wherein:
said third set of stent elements are deployed in a position distally relative to said second set of stent elements by passing said third set of stent elements in a collapsed state through said second set of stent elements in an expanded state.

53. A modular stent graft according to claim 50, further comprising:
a fourth set of stent elements that are disposed adjacent to a distal portion of said leg graft, said distal portion of said leg graft operably disposed within said pant leg section of said bifurcated graft, wherein in an expanded state said fourth set of stent elements interconnect said leg graft to said pant leg section.

54. A modular stent graft according to claim 53, further comprising:
longitudinal stent elements that are disposed external to said exterior surface of said leg graft and that extend between said third set of stent elements and said fourth set of stent elements.

55. A modular stent graft according to claim 50, further comprising:
a ring of stent elements that are disposed distally relative to a distal end of said bifurcated graft element, said ring of stent elements for supporting said bifurcated graft element in the aorta.

* * * * *